US011851676B2

(12) United States Patent
Gopurappilly et al.

(10) Patent No.: US 11,851,676 B2
(45) Date of Patent: Dec. 26, 2023

(54) HUMAN NEURAL PRECURSOR CELLS WITH INDUCIBLE STIM1 KNOCKDOWN

(71) Applicant: NATIONAL CENTRE FOR BIOLOGICAL SCIENCES, Karnataka (IN)

(72) Inventors: Renjitha Gopurappilly, Karnataka (IN); Gaiti Hasan, Karnataka (IN); Bipan Kumar Deb, Karnataka (IN)

(73) Assignee: NATIONAL CENTRE FOR BIOLOGICAL SCIENCES, Karnataka (IN)

( * ) Notice: Subject to any disclaimer, the term of this patent is extended or adjusted under 35 U.S.C. 154(b) by 521 days.

(21) Appl. No.: 16/386,907

(22) Filed: Apr. 17, 2019

(65) Prior Publication Data
US 2020/0017828 A1    Jan. 16, 2020

(30) Foreign Application Priority Data
Apr. 18, 2018 (IN) .............................. 201841014670

(51) Int. Cl.
C12N 15/113 (2010.01)
C12N 15/86 (2006.01)
C12N 5/0793 (2010.01)
C12N 5/074 (2010.01)

(52) U.S. Cl.
CPC ......... *C12N 5/0619* (2013.01); *C12N 5/0696* (2013.01); *C12N 15/113* (2013.01); *C12N 15/86* (2013.01); *C12N 2310/141* (2013.01); *C12N 2740/15041* (2013.01)

(58) Field of Classification Search
CPC .............................. C12N 15/113; C12N 15/86
See application file for complete search history.

(56) References Cited

PUBLICATIONS

Hao et al. "Role of STIM1 in survival and neural differentiation of mouse embryonic stem cells independent of Orai1-mediated Ca2+ entry", Stem Cell Research (2014) 12, 452-466. (Year: 2014).*
Bardo et al., 2006; The role of the endoplasmic reticulum Ca2+ store in the plasticity of central neurons: Trends Pharmacol Sci 27:78-84.
Feske et al., A mutation in Orai1 causes immune deficiency by abrogating CRAC channel function2006 Nature 441: 179-85.
Guemez-Gamboa et al., 2014; Non-Cell-Autonomous Mechanism of Activity-Dependent Neurotransmitter Switching; Neuron 82:1004-1016, synaptogenesis and neurite extension.
Hartmann et al., 2014; STIM1 Controls Neuronal Ca2+ Signaling, mGluR1-Dependent Synaptic Transmission, and Cerebellar Motor Behavior Neuron 82:635-644.
Kawamoto et al., 2012; Physiology and pathology of calcium signaling in the brain; Front Pharmacol Apr. 3.
Liou et al., 2005; STIM is a Ca2+ Sensor Essential for Ca2+-Store-Depletion-Triggered Ca2+ Influx Curr Biol 15:1235-1241.
Majewski and Kuznicki, 2015; SOCE in neurons: Signaling or just refilling? Biochem Biophys 956 Acta—Mol Cell Res 1853:1940-1952.
Marek et al., 2010; cJun phosphorylation integrates calcium spike activity and tlx3 expression to regulate neurotransmitter specification; Neurosci 13:944-950.
Pathak et al., 2015; Store-Operated Calcium Entry through Orai is Required for Transcriptional Maturation of the Flight Circuit in *Drosophila* J Neurosci 35:13784.
Plazas et al., 2013; Activity-dependent competition regulates motor neuron axon pathfinding via PlexinA3; Proc Natl Acad Sci 110:1524-1529.
Roos et al., 2005; STIM1, an essential and conserved component of store-operated Ca2+ channel function; J Cell Biol 169:435-445.
Rosenberg and Spitzer, 2011; Calcium Signaling in Neuronal Development; Cold Spring Harbour 1046 Perspect Biol 3:1-13.
Rusanescu et al., 1995; Calcium Influx Induces Neurite Growth Through a Src-Ras Signaling Cassette; Neuron 15:1415-1425.
Somasundaram A, et. al. 2014; Store-Operated CRAC Channels Regulate Gene Expression and Proliferation in Neural Progenitor Cells; J Neurosci 34:9107-9123.
Toth et al., 2016; Regulation of neurogenesis by calcium signaling; Cell Calcium 59:124-134.
Venkiteswaran and Hasan, 2009; Intracellular Ca2+ signaling and store-operated Ca2+ entry are required in *Drosophila* neurons for flight Proc Natl Acad Sci 106:10326-1033.
Vig et al., 2006; CRACM1 is a Plasma Membrane Protein Essential for Store-Operated Ca2+ EntryScience 312:1220-1223.
Zhang et al., 2006; Genome-wide RNAi screen of Ca2_ influx identifies genes that regulate Ca2_ release-activated Ca2_ channel activity Proc Natl. Acad Sci 103:9357-9362.
Knoth, R., Singec, I., Ditter, M., Pantazis, G., Capetian, P., Meyer, R. P., et al. Murine features of neurogenesis in the human hippocampus across the lifespan from 0 to 100 years. PLoS One ; Jan. 2010 , vol. 5, Issue 1 . e 8809.
Wang, C., Liu, F., Liu, Y. Y., Zhao, C. H., You, Y., Wang, L., et al. Identification and characterization of neuroblasts in the subventricular zone and rostral migratory stream of the adult human brain. Cell Res. Nov. 2011; 21(11): 1534-1550.
Van Praag, H., Schinder, A. F., Christie, B. R., Toni, N., Palmer, T. D., and Gage F. H. (2002). Functional neurogenesis in the adult hippocampus. Nature ,vol. 415, 1030-1034.,Feb. 28, 2002 l © 2002 Macmillan Magazines Ltd.

(Continued)

*Primary Examiner* — James D Schultz
*Assistant Examiner* — James Joseph Graber
(74) *Attorney, Agent, or Firm* — D'Ambrosio & Menon, PLLC; Usha Menon

(57) ABSTRACT

Human Neural precursor cells (hNPCs)/cell lines derived from human pluripotent stem cells have been stably transduced with inducible lentiviral constructs for knockdown of STIM1 thereby changing their gene expression. The said Human Neural precursor cells (hNPCs)/cell lines has selectively inducible knockdown of STIM1 via stable transduction of lentiviral shRNA vector followed by Doxycycline treatment. Human Neural precursor cells (hNPCs)/cell lines with stable knockdown STIM1 exhibits attenuated SOCE with downregulation of genes associated with cell proliferation and upregulation of genes for neural differentiation.

Figure 1:
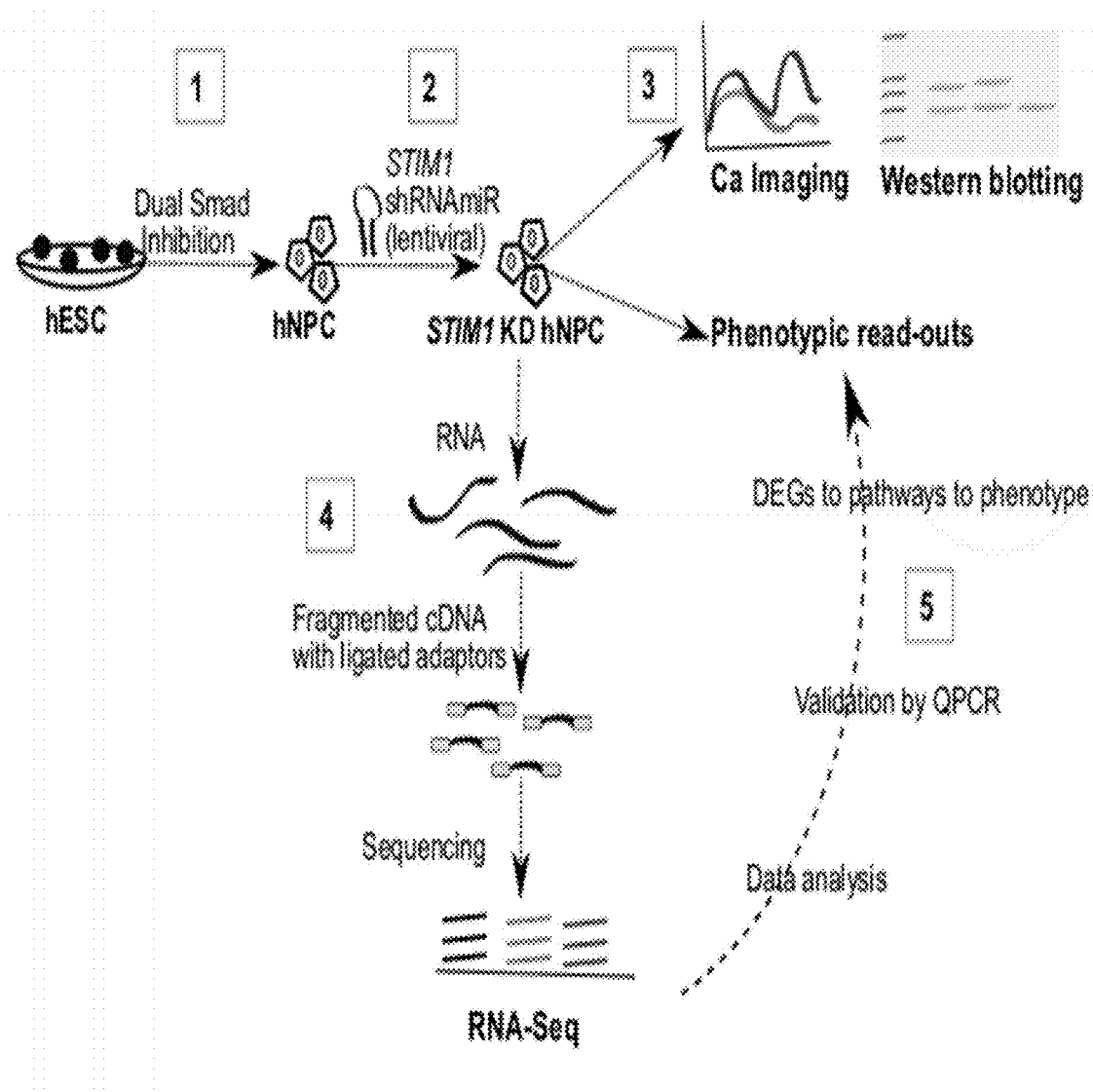

4 Claims, 10 Drawing Sheets
Specification includes a Sequence Listing.

(56) References Cited

PUBLICATIONS

Toni, N., Laplagne, D. A., Zhao, C., Lombardi, G., Ribak, C. E., Gage, F. H., et al. Neurons born in the adult dentate gyrus form functional synapses with target cells. Nat. Neurosci. Aug. 11 (8), 901-907. 2008.

Boldrini, M., Fulmore, C. A., Tartt, A. N., Simeon, L. R., Pavlova, I., Poposka, V., et al. Human hippocampal neurogenesis persists throughout aging. Cell Stem Cell 22, 589-599 Apr. 5, 2018.

Sorrells, S. F., Paredes, M. F., Cebrian-Silla, A., Sandoval, K., Qi, D., Kelley, K. W., et al. (2018). Human hippocampal neurogenesis drops sharply in children to undetectable levels in adults. Nature. Mar. 15, 2018; 555(7696): 377-381.

Ostenfeld, T., Caldwell, M. A., Prowse, K. R., Linskens, M. H., Jauniaux, E., and Svendsen, C. N. Human neural precursor cells express low levels of telomerase in vitro and show diminishing cell proliferation with extensive axonal outgrowth following transplantation. Experimental Neurology; vol. 164, Issue 1, Jul. 2000, pp. 215-226.

Ostenfeld, T., Joly, E., Tai, Y. T., Peters, A., Caldwell, M., Jauniaux, E., et al.). Regional specification of rodent and human neurospheres. Developmental Brain Research vol. 134, Issues 1-2, Mar. 31, 2002, pp. 43-55.

Harrill, J. A., Freudenrich, T. M., Robinette, B. L., and Mundy, W. R. Comparative sensitivity of human and rat neural cultures to chemical-induced inhibition of neurite outgrowth. Toxicol. Appl. Pharmacol. vol. 256, Issue 3, Nov. 1, 2011, pp. 268-280.

Culbreth, M. E., Harrill, J. A., Freudenrich, T. M., Mundy, W. R., and Shafer, T. J. Comparison of chemical-induced changes in proliferation and apoptosis in human and mouse neuroprogenitor cells. vol. 33, Issue 6, Dec. 2012, pp. 1499-151.

Sanai, H., Tramontin, A. D., Quiñones-Hinojosa, A., Barbaro, N. M., Gupta, H., Kunwar, S., et al. Unique astrocyte ribbon in adult human brain contains neural stem cells but lacks chain migration. Nature | vol. 427 Feb. 19, 2004.

Vincent C. Auyeung,Igor Ulitsky,Sean E. McGeary,and David P. Bartel Beyond Secondary Structure: Primary-Sequence Determinants License Pri-miRNA Hairpins for Processing Cell 152, 844-858, Feb. 14, 2013 Elsevier Inc.

Renjitha Gopurappilly,Bipan Kumar Deb,Pragnya Chakraborty and Gaiti Hasan;Stable STIM1 Knockdown in Self-Renewing Human Neural Precursors Promotes Premature Neural Differentiation; Front. Mol. Neurosci., 11 Jun. 11, 2018 p. 1-9.

Knott, S. R. V., Maceli, A. R., Erard, N., Chang, K., Marran, K., Zhou, X., et al. (2014). A computational algorithm to predict shRNA potency. Mol. Cell56, 796-807. doi: 10.1016/j.molcel.2014.10.025.

\* cited by examiner

HUMAN NEURAL PRECURSOR CELLS WITH INDUCIBLE STIM1 KNOCKDOWN

CROSS-REFERENCE TO RELATED APPLICATIONS

This application is related to and claims priority to Indian Patent Application No. 201841014670 filed on Apr. 18, 2018, the contents of which are incorporated by reference herein.

INCORPORATION BY REFERENCE

This application includes a sequence listing in computer readable form (a "txt" file) that is submitted herewith. This sequence listing is incorporated by reference herein as SEQ.ID.NO.1: ULTRA-3374033, SEQ.ID.NO 2: ULTRA-3374029, SEQ.ID.NO. 3: ULTRA-3374031, SEQ.ID.NO. 4: forward primer for GAPDH, SEQ.ID.NO. 5: reverse primer for GAPDH,SEQ.ID.NO. 6: forward primer for STIM1, SEQ.ID.NO. 7: reverse primer for STIM1, SEQ.ID.NO.8: forward primer for UNC5C, SEQ.ID.NO.9: reverse primer for UNC5C. SEQ.ID.NO.10: forward primer for ELAVL3, SEQ.ID.NO.11: reverse primer for ELAVL3, SEQ.ID.NO.12: forwaard primer for DLG4, SEQ.ID.NO.13: reverse primer for DLG4, SEQ.ID.NO.14: forward primer for NFAT4, SEQ.ID.NO.15: reverse primer for NFAT4, SEQ.ID.NO.16: forward primer for LIN28A, SEQ.ID.NO.17: reverse primer for LIN28A, SEQ.ID.NO. 18: forward primer for BAX and SEQ.ID.NO.19: reverse primer for BAX.

FIELD OF THE INVENTION

The present invention relates to a human neural precursor cell (hNPCs) line with selectively inducible knockdown of the STIM1 protein. More specifically, the present invention relates to human neural precursor cells/cell line with knockdown of STIM1, an Endoplasmic Reticulum-localized calcium sensor, regulating intracellular calcium signalling and decreased Store Operated Calcium Entry (SOCE), which thereby decreases the proliferation of hNPCs and induces premature neurogenesis. Said hNPCs derived from human pluripotent stem cells have been stably transduced with inducible lentiviral constructs for knockdown of STIM1 thereby changing the gene expression. Advantageously, the stable STIM1 knockdown human neural precursors and their neural derivatives have utility in studying neurodegenerative diseases directly in human neurons particularly relevant for all neurodegenerative disorders where intracellular calcium signaling is considered causative including Alzheimer's, Huntington's, Parkinson's and Spinocerebellar ataxias. Additionally the said are useful for drug screening and toxicity testing.

BACKGROUND ART

The advent of pluripotent stem cells in the past decade, which includes embryonic stem cells (ESC) and induced pluripotent stem cells (iPSCs) and their neural derivatives, has allowed direct cellular and molecular analysis of human cell-derived brain progenitors as well as differentiated neurons. From cellular studies in other organisms it is evident that $Ca^{2+}$ signaling affects a range of neural activities during development including neurotransmitter specification (Marek et al., 2010 Neurosci 13:944-950; Plazas et al., 2013 Proc Natl Acad Sci 110:1524-1529; Guemez-Gamboa et al., 2014 Neuron 82:1004-1016), synaptogenesis and neurite extension (Rusanescu et al., 1995 Neuron 15:1415-1425; Rosenberg and Spitzer, 2011 Cold Spring Harbour 1046 Perspect Biol 3:1-13; Kawamoto et al., 2012 Front Pharmacol 3 APR). Besides well-documented modes of $Ca^{2+}$ entry in neuronal cells through ligand and voltage gated $Ca^{2+}$ channels, it is evident that ER-driven store-operated $Ca^{2+}$ entry (SOCE), also functions in neurons (Bardo et al., 2006, Trends Pharmacol Sci 27:78-84). Store-operated $Ca^{2+}$ entry (SOCE) based on the interaction of STIM1 proteins that sense $Ca^+$ levels in the ER (Liou et al., 2005, Curr Biol 15:1235-1241; Roos et al., 2005, J Cell Biol 169:435-445) and the Orai $Ca^{2+}$ channel in the plasma membrane (Feske et al., 2006 Nature 441: 179-85; Vig et al., 2006 Science 312:1220-1223; Zhang et al., 2006 Proc Natl. Acad Sci 103:9357-9362) were first described in non-excitable cells. More recently it has also been characterized in excitable cells (Venkiteswaran and Hasan, 2009 Proc Natl Acad Sci 106:10326-1033; Hartmann et al., 2014 Neuron 82:635-644; Pathak et al., 2015, J Neurosci where significant roles for intracellular $Ca^+$ stores and potentially SOCE have been suggested in neurogenesis and neural development (Toth et al., 2016, Cell Calcium 59:124-134). Neuronal SOCE has thus been recognized as an important mechanism that neurons use to replenish $Ca^{2+}$ stores during cell activation. As in non-excitable cells SOCE might also initiate specific signaling pathways in NPCs and differentiated neurons (Majewski and Kuznicki, 2015 Biochim Biophys 956 Acta—Mol Cell Res 1853:1940-1952). Most studies till date have used murine neuronal cell lines/primary cells to understand different aspects of store operated calcium entry (SOCE) in the context of neurological disorders and neurodegeneration. Domenichini F. et. al. in Stem Cells (2018 36:761-774. doi: 10.1002/stem.2786) relates that the subventricular zone (SVZ) is the major stem cell niche in the brain of adult mammals. Within this region, neural stem cells (NSC) proliferate, self-renew and give birth to neurons and glial cells. Previous studies underlined enrichment in calcium signalling-related transcripts in adult NSC. Because of their ability to mobilize sustained calcium influxes in response to a wide range of extracellular factors, store-operated channels (SOC) appear to be, among calcium channels, relevant candidates to induce calcium signalling in NSC whose cellular activities are continuously adapted to physiological signals from the microenvironment. By Reverse Transcription Polymerase Chain Reaction (RT-PCR), Western blotting and immunocytochemistry experiments, it was demonstrated that SVZ cells express molecular factors known to build up SOC, namely transient receptor potential canonical 1 (TRPC1) and Orai1, as well as their activator stromal interaction molecule 1 (SUMO. Calcium imaging reveals that SVZ cells display store-operated calcium entries. Pharmacological blockade of SOC with SKF-96365 or YM-58483 (also called BTP2) decreases proliferation, impairs self-renewal by shifting the type of SVZ stem cell division from symmetric proliferative to asymmetric, thereby reducing the stem cell population. Brain section immunostainings show that TRPC1, Orai1, and STIM1 are expressed in vivo, in SOX2-positive SVZ NSC. Injection of SKF-96365 in brain lateral ventricle diminishes SVZ cell proliferation and reduces the ability of SVZ cells to form neurospheres in vitro. The said study combining in vitro and in vivo approaches uncovered a major role for SOC in the control of SVZ NSC population and opens new fields of investigation for stem cell biology in health and disease.

Somasundaram A, et. al. (2014, J Neurosci 34:9107-9123) discloses that Calcium signals regulate many critical processes during vertebrate brain development including neurogenesis, neurotransmitter specification, and axonal outgrowth. The study reports that embryonic and adult mouse neural stem/progenitor cells (NSCs/NPCs) exhibit store-operated $Ca^{2+}$ entry (SOCE) mediated by $Ca^{2+}$ release-activated $Ca^{2+}$ (CRAC) channels. SOCE in NPCs was blocked by the CRAC channel inhibitors $La^{3+}$, BTP2, and 2-APB and Western blots revealed the presence of the canonical CRAC channel proteins STIM1 and Orai1. Knockdown of STIM1 or Orai1 significantly diminished SOCE in NPCs, and SOCE was lost in NPCs from transgenic mice lacking Orai1 or STEW and in knock-in mice expressing the loss-of-function Orai1 mutant, R93W. Therefore, STIM1 and Orai1 make essential contributions to SOCE in NPCs. SOCE in NPCs was activated by epidermal growth factor and acetylcholine, the latter occurring through muscarinic receptors. Activation of SOCE stimulated gene transcription through calcineurin/NFAT (nuclear factor of activated T cells) signaling through a mechanism consistent with local $Ca^{2+}$ signaling by $Ca^{2+}$ microdomains near CRAC channels. Importantly, suppression or deletion of STIM1 and Orai1 expression significantly attenuated proliferation of embryonic and adult NPCs cultured as neurospheres and, in vivo, in the subventricular zone of adult mice. These findings show that CRAC channels serve as a major route of $Ca^{2+}$ entry in NPCs and regulate key effector functions including gene expression and proliferation, indicating that CRAC channels are important regulators of mammalian neurogenesis.

In spite of the above studies concerning block of SOC in the rodent SVZ NSC there has been a continuing need in the art to make advancements concerning regulation of human neural precursor cells to maintain their proliferative potential and generate neurons or glia in a spatio-temporal manner which is important in the context of multiple neurological and psychiatric disease conditions.

OBJECTS OF THE INVENTION

It is thus the basic object of the present advancement to provide hNPCs/cell line with knockdown of STIM1 protein regulating intracellular calcium signalling and decreased Store Operated Calcium Entry (SOCE).

Another object of the present invention is to provide hNPCs/cell line with knockdown of STIM1 protein that can be used to generate multiple classes of differentiated human neurons to model neurodegenerative diseases with altered intracellular calcium signaling.

Another object of the present invention is to provide hNPCs/cell line with knockdown of STIM1 protein with decreased proliferation of said hNPCs and induced premature neurogenesis/differentiation.

A further object of the present invention is to provide genetically modified hNPCs and their derivatives to study the effect of intracellular calcium changes on neural precursors, early neural progenitors, immature neurons, mature neurons and aged neurons.

A still further object of the present invention is to provide for genetically modified hNPCs and their derivatives to understand the mechanism of neurological disorders with altered calcium signaling.

Thus according to the basic aspect of the present invention there is provided STIM1 knockdown hNPCs with down-regulation of pathways associated with cell proliferation and concomitantly an up-regulation of genes for neural differentiation.

Yet another object of the present invention provides for Human Neural precursor cells (hNPCs)/cell lines wherein said inducible knockdown of STIM1 comprises Doxycycline, Tetracycline or any derivatives preferably Doxycycline based selectively inducible knockdown of STIM1.

SUMMARY OF INVENTION

Thus according to the basic aspect of the present invention there is provided human Neural precursor cells (hNPCs)/cell lines including induced capability of knockdown of STIM1 protein comprising lentiviral constructs with at least selective knockdown of STIM1 enabling changing the gene expression related to the STIM1 protein selectively as an Endoplasmic Reticulum-localized calcium sensor, regulating intracellular calcium signalling and decreased Store Operated Calcium Entry (SOCE).

According to another aspect of the present invention there is provided for Human Neural precursor cells (hNPCs)/cell lines as above comprising a stably knocked-down STIM-1 or selectively inducible knockdown of STIM1.

According to yet further aspect of the present invention there is provided for human Neural precursor cells (hNPCs)/cell lines as claimed in claim 2 wherein said selectively inducible knockdown of STIM1 comprises Doxycycline, Tetracycline or any derivatives preferably Doxycycline based selectively inducible knockdown of STIM1.

A still further aspect of the present invention provides for human Neural precursor cells (hNPCs)/cell lines comprising transfer vector which is co-transfected with lentivirus based second generation packaging plasmids as the viral genome and code for inducible shRNA-mir against STIM1 and selection cassette adapted to integrate into the target cell's genome.

In a further aspect the present invention provides for Human Neural precursor cells (hNPCs)/cell lines including knockdown of STIM1 comprising Lentiviral shRNA vector transduced in Human Neural precursor cells (hNPCs)/cell lines for stable knockdown of STIM1 for attenuated SOCE with down-regulation of genes associated with cell proliferation and/or up-regulation of genes for neural differentiation.

Human Neural precursor cells (hNPCs)/cell lines including inducible knockdown of STIM1 as claimed in anyone of claim 1 or 2 derived from pluripotent stem cell lines including human embryonic stem cell line (hESCs) and human induced pluripotent stem cell line.

Another aspect of the present invention provides for Human Neural precursor cells (hNPCs)/cell lines comprising mixture of shRNA-miRs for maximal STIM1 knockdown.

Yet another aspect of the present invention provides for Human Neural precursor cells (hNPCs)/cell lines with STIM1 knockdown achieved by lentiviral transduction wherein lentiviral transfer vector (pZIP) is co-transfected with packaging vectors (pCMV-dR8.2 and pCMV-VSVG from Addgene RRID:SCR_002037) encoding the env, gag and pol protein into a packaging cell line (HEK293T-ATCC Cat #CRL-3216, RRID:CVCL_0063) to get viruses for transduction.

In a further aspect the present invention provides Human Neural precursor cells (hNPCs)/cell lines with STIM1 knockdown which exhibits gene expression including nervous system development (GO:0007399), membrane depolarization (GO:0051899), neuron cell-cell adhesion (GO:0007158) and chemical synaptic transmission (GO:0007268) consistent with neuronal differentiation.

Yet another aspect of the present invention provides Human Neural precursor cells (hNPCs)/cell lines with STIM1 knockdown which exhibits down-regulated genes expression including reduced cell proliferation including rRNA processing (GO:0006364), cell proliferation (GO: 0008283), G1/S transition of mitotic cell cycle (GO: 0000082) and DNA replication (GO:0006260).

A still further aspect of the present invention provides for Human Neural precursor cells (hNPCs)/cell lines characterized by rapid spontaneous differentiation into branched neurites and sparse cell clustering upon STIM1 knockdown.

In a further aspect, the present invention provides for Human Neural precursor cells (hNPCs)/cell lines adapted selectively (i) to form neurospheres having of reduced size and (ii) having 50% reduction of neurosphere numbers upon STIM1 knockdown.

One aspect of the present invention provides for Human Neural precursor cells (hNPCs)/cell lines with STIM1 knockdown comprising upregulated transcript levels of neuronal (NPY, NPTX2, DLG4, NLGN4X, NRXN2, CEND1, NEFH, NEUROG2, NEUROG1) and some early glial markers (HESS, SLC1A3, CD44, PDGFRA) including RNAseq data (GSE109111).

A still further aspect of the present invention provides for Human Neural precursor cells (hNPCs)/cell lines wherein the sequences coding for the STIM1-shRNA-miR comprises a mixture of STIM1-ULTRA-3374033 (TAATAT-TGCACCTCCACCTCAT) SEQ. ID. NO.:1, ULTRA-3374029(TTTATGATCTACATCATCCAGG)-SEQ. ID. NO.:2 and ULTRA-3374031 (TCCAGTGAGTG-GATGCCAGGGT) SEQ. ID. NO.:3.

Yet another aspect of the present invention provides a process for manufacture of Human Neural precursor cells (hNPCs)/cell lines having selective knockdown of STIM1 comprising steps of:

Providing Human Neural precursor cells (hNPCs)/cell lines; and

Carrying out step of gene expression modulation involving lentiviral transduction for STIM1 protein for desired selective knockdown of STIM1, functioning as an Endoplasmic Reticulum-localized calcium sensor, regulating intracellular calcium signalling and decreased Store Operated Calcium Entry (SOCE), In a still further aspect of the present invention it its provided a process for manufacture of Human Neural precursor cells (hNPCs)/cell lines having selective knockdown of STIM1 wherein said lentiviral transduction for STIM1 protein comprises inducible vectors adapted for regulated expression of shRNA-mir involving selectively Doxycycline, Tetracycline or any derivatives preferably Doxycycline based selectively inducible knockdown of STIM1.

A further aspect of the present invention provides a process as comprising:

i. co-transfecting lentiviral transfer vector (pZIP) with the desired packaging vectors;
ii. harvesting and concentrating the viral particles;
iii. applying to said NPCs such as to induce desired shRNA expression of maximal STIM1 knockdown.

Another aspect of the present invention provide a process comprising the steps of i. Treating hNPCs with the lentiviral transfer vector (pZIP) and code for the shRNA-mir against STIM co-transfected with the selected packaging vectors (pCMV-dR8.2 and pCMV-VSVG) containing the sequences that packages as the viral genome and selection cassette that integrates into the target cell's genome.

ii. Passaging the said transduced NPCs for at least 5 passages with Doxycycline thus inducing stable STIM1 knockdown in hNPC cells/cell line.

In one aspect the present invention provides a process wherein the lentiviral transfer vector (pZIP) comprising a mixture of sequences: STIM1-ULTRA-3374033 SEQ. ID. NO.:1, ULTRA-3374029 SEQ. ID. NO.:2 and ULTRA-3374031–(SEQ. ID. NO.:3 is co-transfected with the desired packaging vectors.

In accordance with another aspect of the present invention there is provided a kit for selectively inducing capability of knockdown of STIM1 protein comprising Human Neural precursor cells (hNPCs)/cell lines including induced capability of knockdown of STIM1 protein comprising lentiviral constructs with selective knockdown of STIM1 favouring changes in the gene expression related to the STIM1 protein which functions selectively as an Endoplasmic Reticulum-localized calcium sensor, regulating intracellular calcium signalling and decreased Store Operated Calcium Entry (SOCE), and Doxycycline for selectively inducible knockdown of STIM1.

According to another aspect there is provided a kit wherein said Human neural precursor cells include cells derived from pluripotent stem cell lines including human embryonic stem cell line (hESCs) and induced pluripotent stem cell line and comprising transfer vector which is co-transfected with lentivirus based second generation packaging plasmids as the viral genome and code for inducible shRNA-mir against STIM1 and selection cassette adapted to integrate into the target cell's genome.

According to another aspect of the present invention there is provided a kit as above comprising mixture of shRNA-miRs for maximal STIM1 knockdown.

According to another aspect of the present invention there is provided a kit as above wherein lentiviral transfer vector (pZIP) is co-transfected with packaging vectors (pCMV-dR8.2 and pCMV-VSVG from Addgene RRID:SCR 002037) encoding the env, gag and pol protein into a packaging cell line (HEK293T-ATCC Cat #CRL-3216, RRID:CVCL_0063).

According to yet another aspect of the present invention there is provided for use of human neural precursor cells line with induced STIM1 knockdown as above selectively for (i) investigating STIM1 function and SOCE in neurodevelopmental, neurodegenerative and psychiatric disorders (ii) study disorders with aberrant NPC regulation such as Rett's syndrome, schizophrenia (iii) study latestage disorders such as Parkinson's disease, Alzheimer's disease and Huntington's disease.

According to yet further aspect of the present invention there is provided a method of studying the temporal functions of STIM1 protein in human NPCs, differentiated neurons and glia comprising the step of:

involving human neural precursor cells line with induced STIM1 knockdown as claimed in anyone of claims 1 to 4;

and selectively adding Doxycycline, Tetracycline or any Tetracycline-derivatives preferably Doxycycline to induce STMI knock down or withdrawing Doxycycline, Tetracycline or any Tetracycline-derivatives preferably Doxycycline to restore protein level of STMI respectively for the study.

Thus according to the above disclosed advancement, small molecule induced hNPCs are derived from undifferentiated human embryonic stem cell line (hESCs)/induced pluripotent stem cell line. The said cells through lentiviral transductuion were successfully knocked down for STIM1, an essential element of SOCE, to obtain expandable stable STIM1 knockdown hNPC cell lines. More specifically the small molecule derived hNPCs are transduced with STIM1 shRNA-miR.

As would be further illustrated hereunder, $Ca^{2+}$ imaging and immunoblots confirmed STIM1 knockdown and the attenuation of SOCE. To investigate cellular and molecular changes brought about by loss of SOCE RNAseq analyses of the STIM1 knockdown NPCs and their appropriate vector controls were performed that helped to identify significant changes in gene expression.

Also demonstrated hereunder are changes in expression levels of selected genes, identified by RNAseq, being further validated by real-time PCR. Moreover, the advancement traverses the functional significance of SOCE-regulated changes in gene expression, Gene Ontology analyses were performed and a set of enriched biological pathways were identified that underwent significant up or down-regulation.

Importantly, these pathways are directed to help design experiments for phenotypic/functional characterization of the STIM1 knockdown NPCs. Such experiments based on the identified GO pathways, can further corroborate a cell fate change in STIM1 knockdown NPCs. The statistics and p-value of the bioinformatics analyses and wet lab experiments are provided in the corresponding segments.

DETAILED DESCRIPTION OF THE INVENTION

As discussed herein before the present invention provides for a human NPCs (hNPCs) with knockdown of STIM1 exhibiting attenuated SOCE. Global transcriptomic analysis of STIM1 knockdown hNPCs revealed change in the gene expression involving down-regulation of pathways associated with cell proliferation and concomitantly an up-regulation of genes for neural differentiation. These changes in gene expression correlated with reduced proliferation and early neural differentiation in STIM1 knockdown hNPC cultures derived from pluripotent stem cells indicate that loss of SOCE in vivo could result in cessation of sufficient hNPCs, required for normal brain development.

The said hNPCs modified by STIM1 knockdown for attenuated SOCE thus provide a tool to understand the diseases with altered calcium signaling using neural precursors as a starting material which can be differentiated into neurons and glia.

All experiments, performed with hESC cell lines, were approved by the Institutional Committee for Stem Cell Research, registered under the National Apex Committee for Stem Cell Research and Therapy, Indian Council of Medical Research, Ministry of Health, New Delhi.

The advantages and utility of the present invention is further illustrated by way of the accompanying figures and following non-limiting examples. The key findings of the present advancement was validated in another pluripotent stem cell type, an induced pluripotent stem cell (iPSC) line NIH1.

BRIEF DESCRIPTION OF NON-LIMITING ACCOMPANYING FIGURES

FIG. 1 illustrates the steps of Experimental design.

Figure 2A:
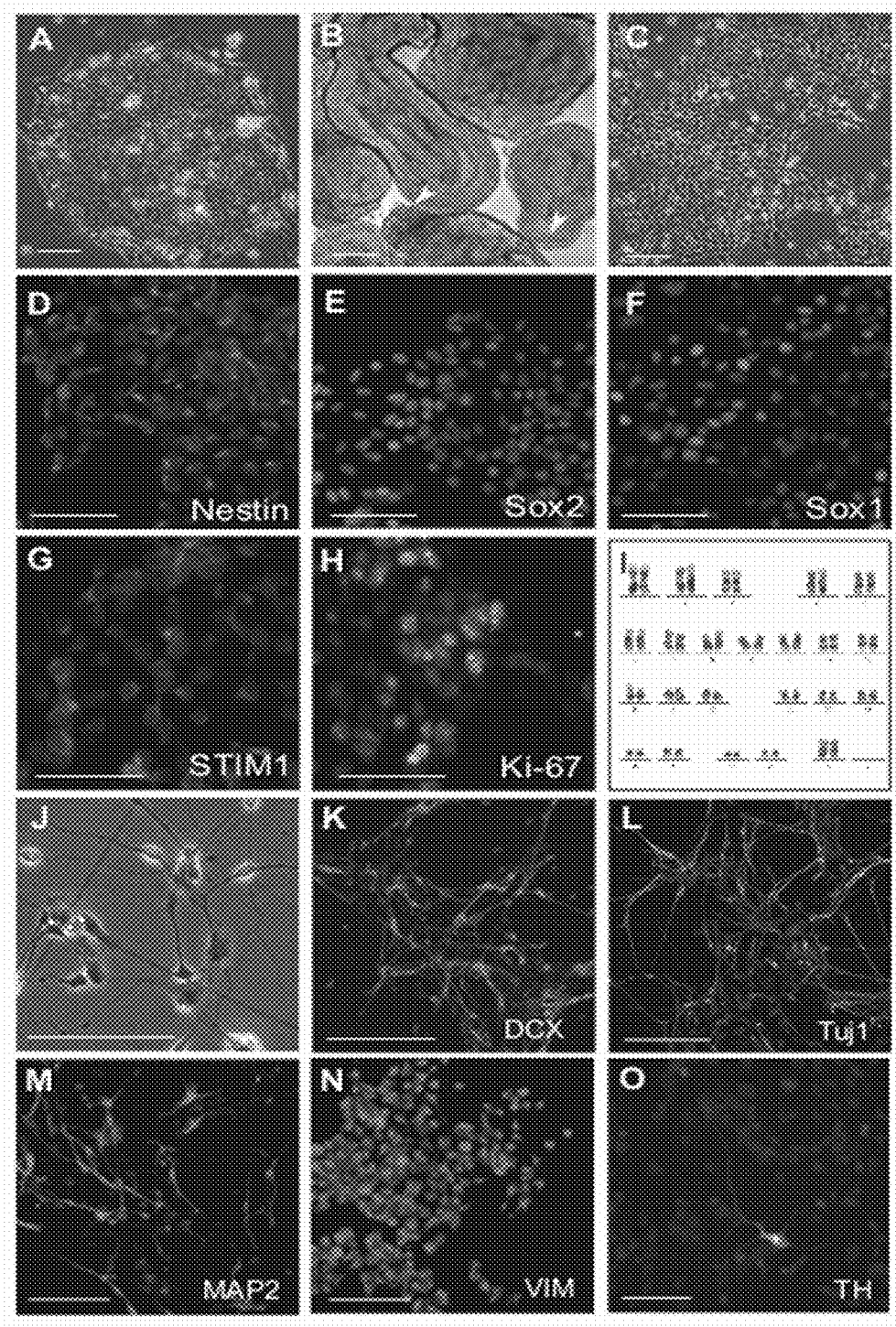

FIG. 2A illustrates Derivation of neural precursor cells (NPC) from hESC. Phase contrast images of (A) hESC colony grown on matrigel (B) Day 4 EBs showing epithelial outgrowths (white arrowheads) when grown in the presence CHIR99021, a GSK 3β inhibitor and Purmorphamine, an activator of Shh pathway (C) Neural precursor cells (NPCs) at passage 5, three days after split. Immunostaining of NPCs with antibodies raised against the neural stem/precursor cell markers as indicated (D) Nestin (E) Sox1 (F) Sox2. NPCs showing robust expression of (G) STIM1 protein, the ER calcium sensor and (H) Ki-67, a proliferation marker (I) Karyogram of NPCs at passage 10 showing a normal karyotype (XX). Differentiation of NPCs into neural derivatives where cells were allowed to spontaneously differentiate for 10 to 14 days, (J) Phase contrast image of a day 12 spontaneously differentiating NPC culture, immunostained for the neuronal markers (K) Dcx (L) Tuj 1 (M) MAP2 and the astroglial progenitor marker (N) Vimentin. (0) TH positive dopaminergic neuron after 21 days in culture. Nuclei are counterstained with DAPI in all immunostaining panels. Scale bars are 100 µm (A-H) and 50 µm (K-O). Representative images are from 2-4 independent experiments.

Figure 2B:
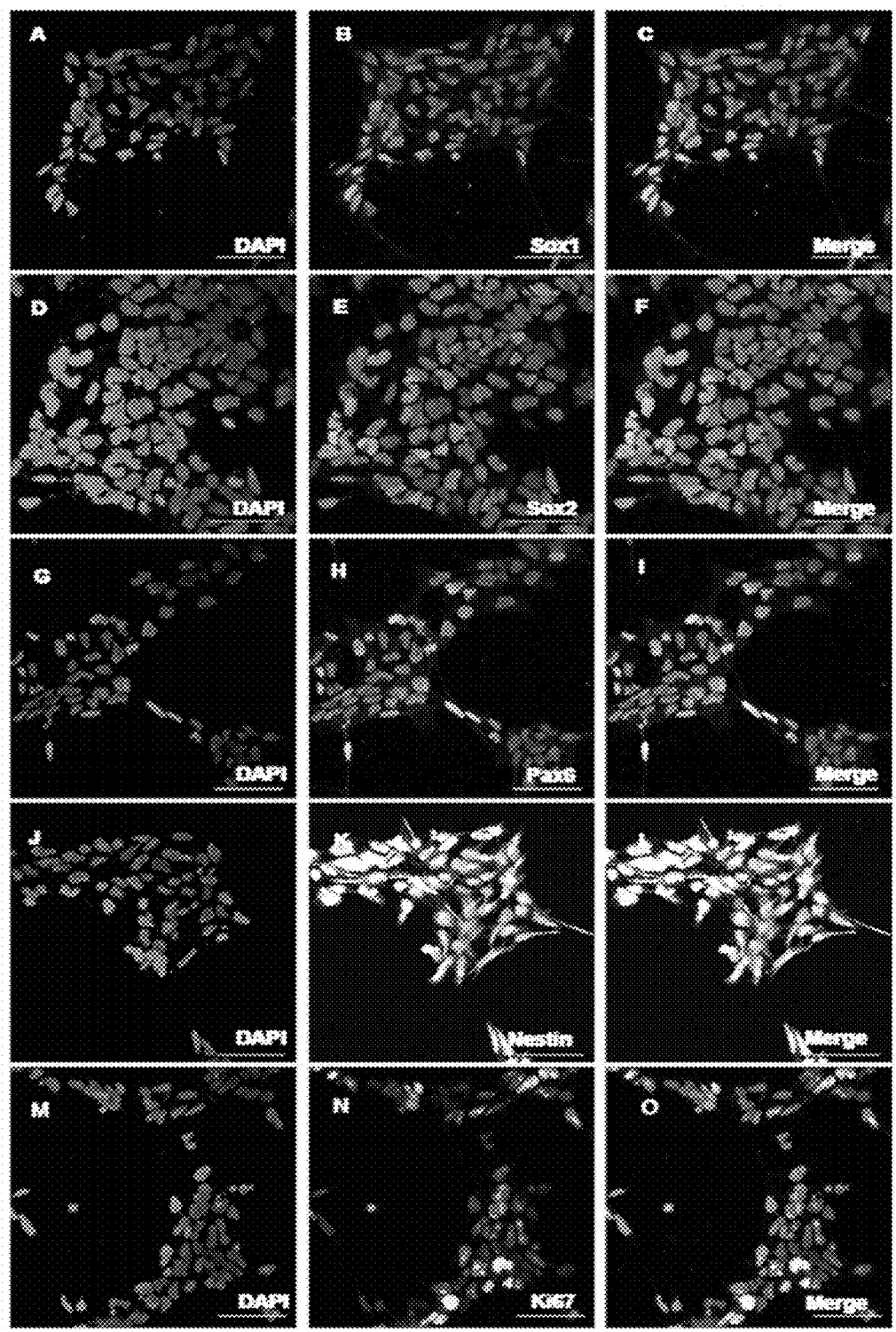

FIG. 2B illustrates Derivation of neural precursor cells (NPC) from iPSC. Immunostaining of NPCs with antibodies raised against the neural stem/precursor cell markers as indicated (A) Sox1 (B) Sox2 (C) Pax6 (D) Nestin and (E) Ki-67, a proliferation marker. Nuclei are counterstained with DAPI in all immunostaining panels. Scale bars are 50 µm.

Figure 3A:
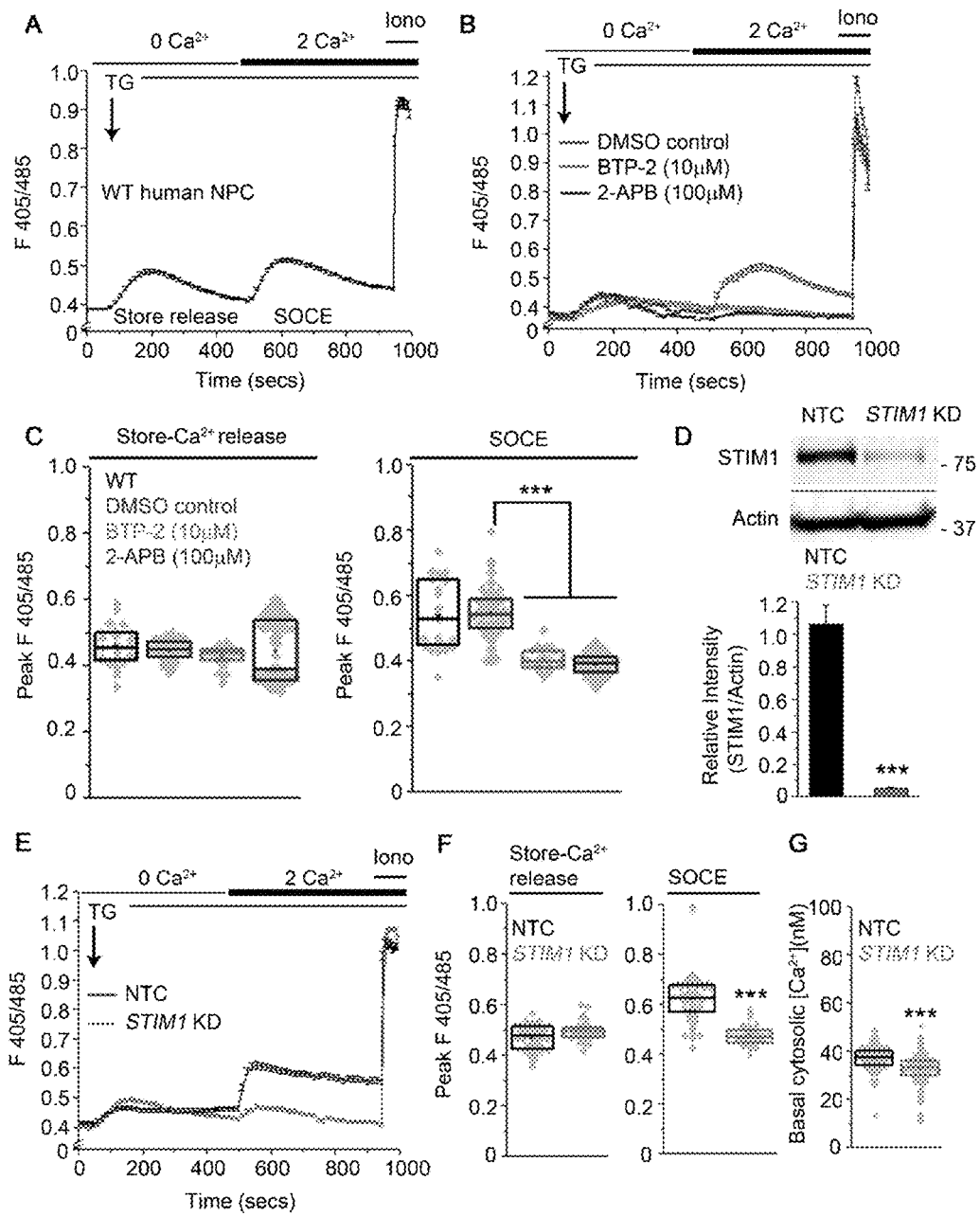

FIG. 3A illustrates Knock-down of STIM1 attenuates SOCE in human NPCs. (A, B) $Ca^{2+}$-responses during ER-store release and SOCE induced by Thapsigargin (TG, 10 µM) measured using the ratiometric $Ca^{2+}$-indicator indo-1-AM in wild-type (WT) hNPCs (A) or hNPCs treated with pharmacological inhibitors of SOCE, BTP-2 and 2-APB at the indicated concentrations or DMSO as a solvent control (B). Each trace represents the mean+SEM for 25-100 cells. Ionomycin (Iono, 10 µM) was added at the end of each imaging to determine the peak F405/485 ratio obtained after saturation of the Ca'-indicator with $Ca^{2+}$ (C) Box plots quantifying the peak F405/485 values for store-release and SOCE in the indicated treatment conditions. Mann-Whitney U test with Bonferroni correction. $p=1.819 \times 10^{-23}$ for DMSO control compared to BTP-2 treatment and $p=1.442 \times 10^{-45}$ for DMSO control compared to 2-APB treatment (D) (Top) A representative Western blot showing levels of STIM1 protein in hNPCs transduced with an NTC (non-targeting control) or an sh-RNA targeting STIM1 (STIM1 KD). Actin serves as the loading control. (Bottom) Quantification of STIM1 band intensities normalized to the loading control Actin from three independent biological replicates (p=0.00069, Student's t-test). (E) $Ca^{2+}$-responses during store-release and SOCE in hNPCs transduced with NTC and STIM1 KD. (F) Box plots quantifying the peak F405/485 values for store-release and SOCE in the indicated genotypes. Peak F405/485 for store-release were not significantly different between NTC and STIM1 KD NPCs. p=0.0001 for peak F405/485 during SOCE compared between NTC- and STIM1 KD NPCs (G) Quantification of basal cytosolic [$Ca^{2+}$] values using Fura-2-AM in NTC and STIM1 KD NPCs ($p=1.115 \times 10^{-8}$. Mann-Whitney U test. *** indicates p<0.001).

Figure 3B:
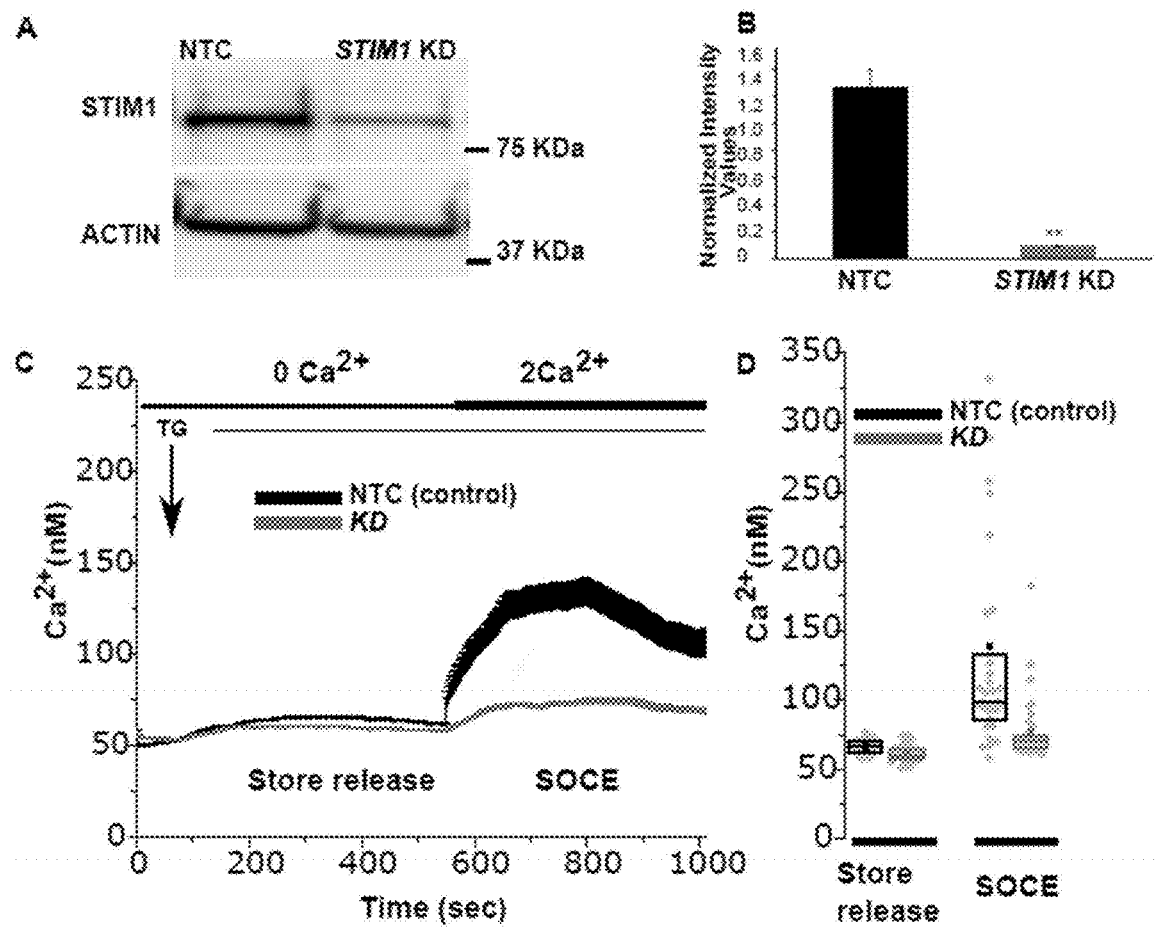

FIG. 3B illustrates Knock-down of STIM1 attenuates SOCE in human iPSC derived NPCs. (A) A representative Western blot showing levels of STIM1 protein in iPSC derived NPCs transduced with an NTC (non-targeting control) or an sh-RNA targeting STIM1 (STIM1 KD). Actin serves as the loading control. (B) Quantification of STIM1 band intensities normalized to the loading control Actin from three independent biological replicates (p=0.009, Student's t-test). (C) $Ca^{2+}$ changes during ER-store depletion using Thapsigargin, TG (10 µM) and SOCE after $Ca^{2+}$ add-back. Fura-2 was used as an indicator. The trace shows the mean [Ca$^{2+}$]±SEM from >35 cells. (D) Box plot quantifying the peak store-release and SOCE in hNPCs. Ratio of F340 and F380 (F340/F380) for each time point was measured and calibrated into [Ca$^{2+}$] by using the Grynkiewicz equation as follows:

$$[Ca^{2+}](nM)=K_d \times \beta \times (R-R_{min})/(R_{max}-R),$$

where $K_d$ for Fura-2 in human cells=225 nM, β refers to scaling factor and R refers to F340/F380 ratio at a particular time point. $R_{min}$ refers to the minimum F340/F380 obtained after addition of 10 mM EGTA to maximally chelate most of free cytosolic Ca$^{2+}$. $R_{max}$ refers to the maximum F340/F380 obtained after addition of Ionomycin (10 μM) in presence of 10 mM extracellular Ca$^{2+}$. This results in saturation of the Fura-2 with Ca$^{2+}$ and hence gives the maximum possible value of R.

Figure 4:
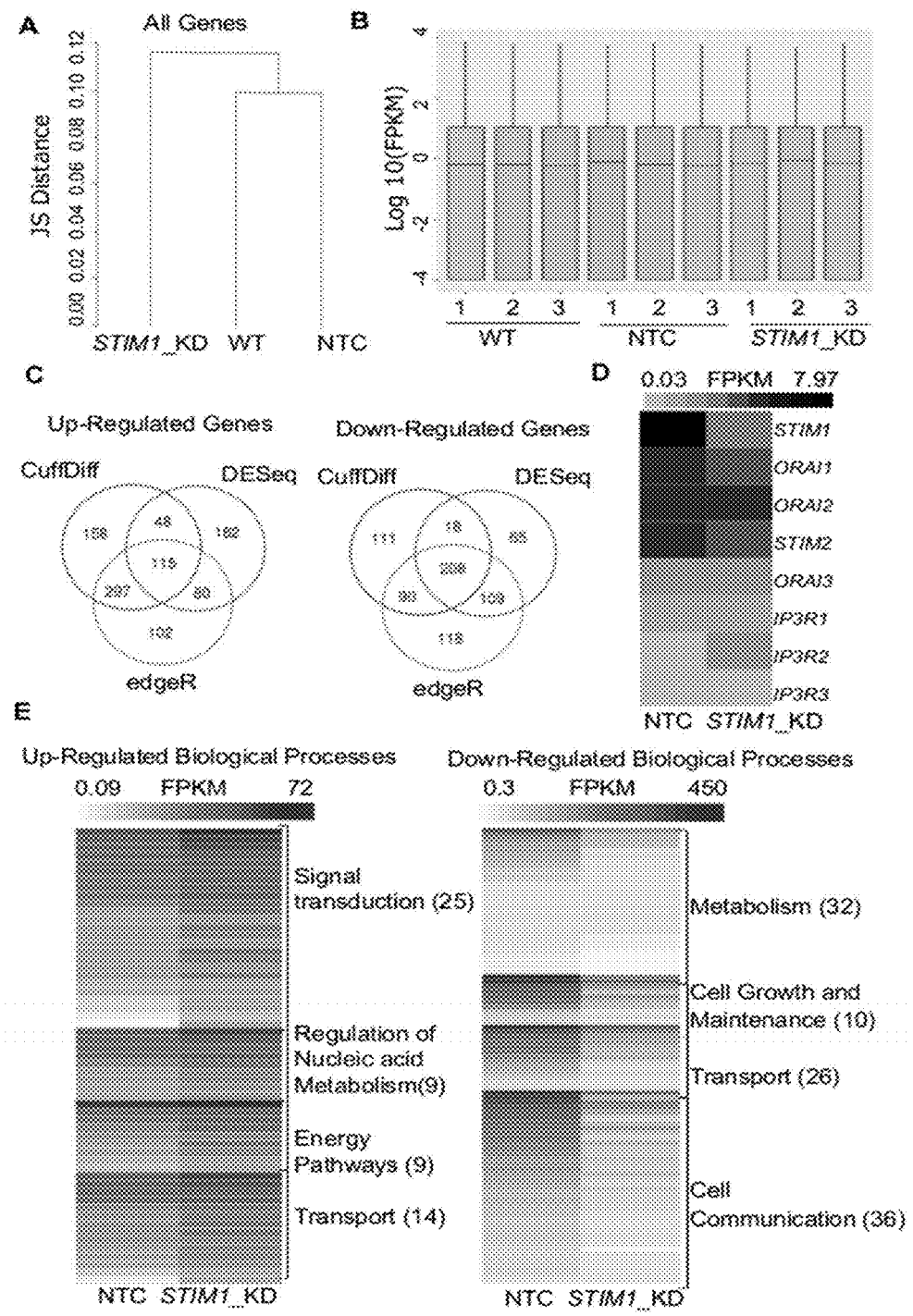

FIG. 4 illustrates Transcriptome analysis reveals global level changes in NPCs on STIM1 knockdown: (A) A dendrogram of Jensen-Shannon divergences analyzing the pattern of gene expression between wild type, NTC and STIM1 knockdown NPCs. Hierarchical clusterin showing the STIM1 knockdown cells to form a separate cluster (B) Box plots indicating the distribution of reads across all the samples sequenced (C) Venn Diagrams representing the number of up and down regulated genes in the STIM1 knockdown NPCs. Genes were tested for differential expression according to Cuffdiff (blue), DESeq (red), and edgeR (green), intersection of genes that were considered differentially transcribed in comparison to control cells were used for further analysis (D) Normalized read counts of the differentially expressed genes involved in SOCE in NTC and STIM1 knockdown conditions represented as a heat map; FPKM—Fragments Per Kilobase per Million reads (**p=0.006; two-tailed t-test) (E) Functional gene enrichment analysis performed in FunRich with genes in the intersection (115 and 208 downregulated) showing biological processes which are differentially regulated in the STIM1 knockdown NPCs based on FPKM values. The number in parentheses represents the number of genes associated with each process in the data set. Three biological replicates per condition were run for RNAseq.

Figure 5:
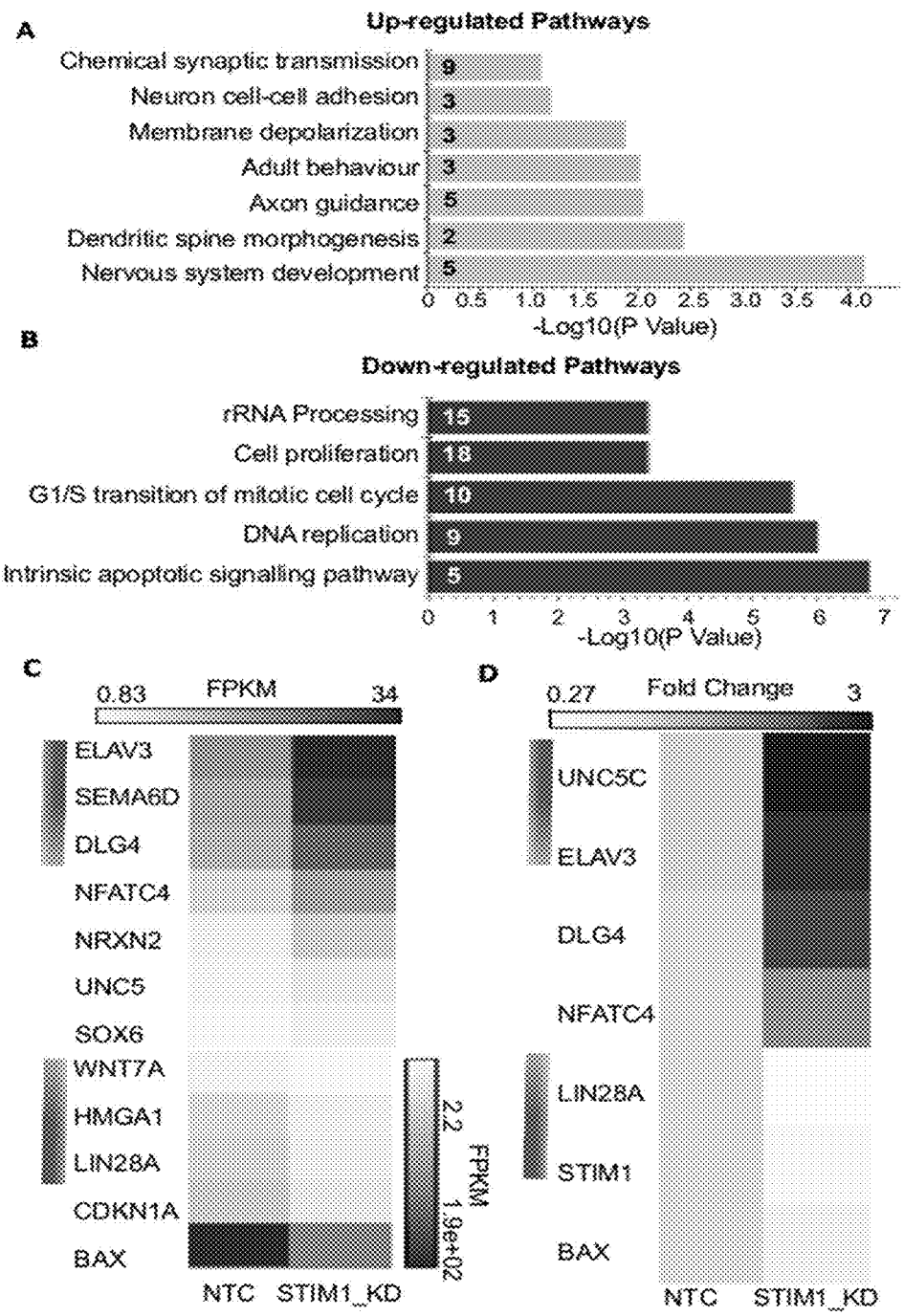
Figure 6A:
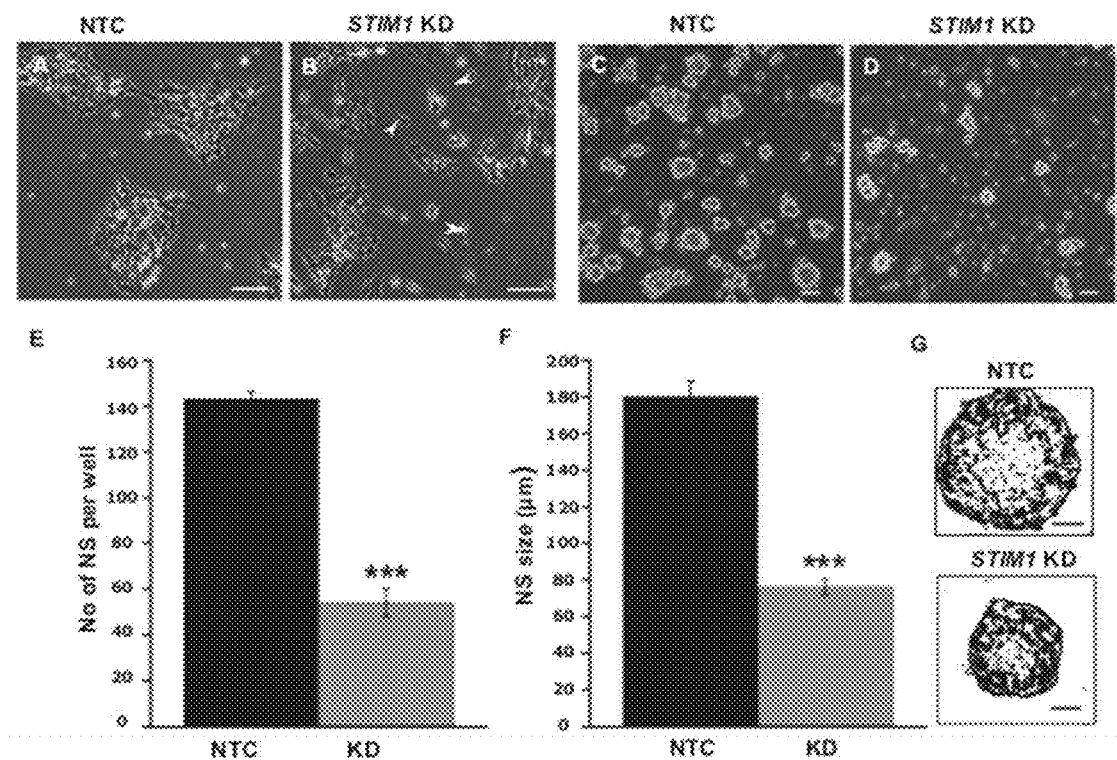

FIG. 5 illustrates Biological pathways affected by STIM1 knockdown in NPCs. Genes that were differentially expressed between NPCs with or without STIM1 knockdown were identified using an enrichment analysis using the DAVID web server (A) Gene-GO term enrichment analysis by DAVID highlighting the most relevant upregulated biological pathways based on the gene IDs, Each bar represents the Fisher Exact P-Value associated with the corresponding enriched pathway and the number in each bar denotes the number of genes involved in each pathway (B) GO terms downregulated in the STIM1 knockdown NPCs based on the gene IDs. Each bar represents the Fisher Exact P-Value associated with the corresponding enriched pathway and the number in each bar denotes the number of genes involved in each pathway (C) Heat map representing normalized read counts of some of the differentially expressed genes in the control and STIM1 knockdown NPCs (D) Heat map representing fold changes of the indicated genes, as validated by qPCR (p<0.05). Four independent samples were used for validation of the RNAseq using RT-PCR. FPKM—Fragments Per Kilobase per Million reads FIG. 6A illustrates STIM1 knockdown represses proliferation of NPCs (A) Control (NTC transduced) cells expressing ZsGreen (B) STIM1 knockdown NPCs undergo spontaneous differentiation as evident by the presence of neurite-like processes and branches (C-D) Neurosphere forming assay (NSA) of NTC and STIM1 knockdown NPCs at 48h (E) Quantification of neurosphere (NS) numbers per well after a week of seeding NTC and STIM1 knockdown NPCs (n=3, p=0.0008) (F) Quantification of NS size in microns (μm) at day 7 (n=4, p=0.00067) (G) Skeletonized (ImajeJ) NS to show the size difference at day 7 of representative NTC and STIM1 knockdown.

Figure 6B:
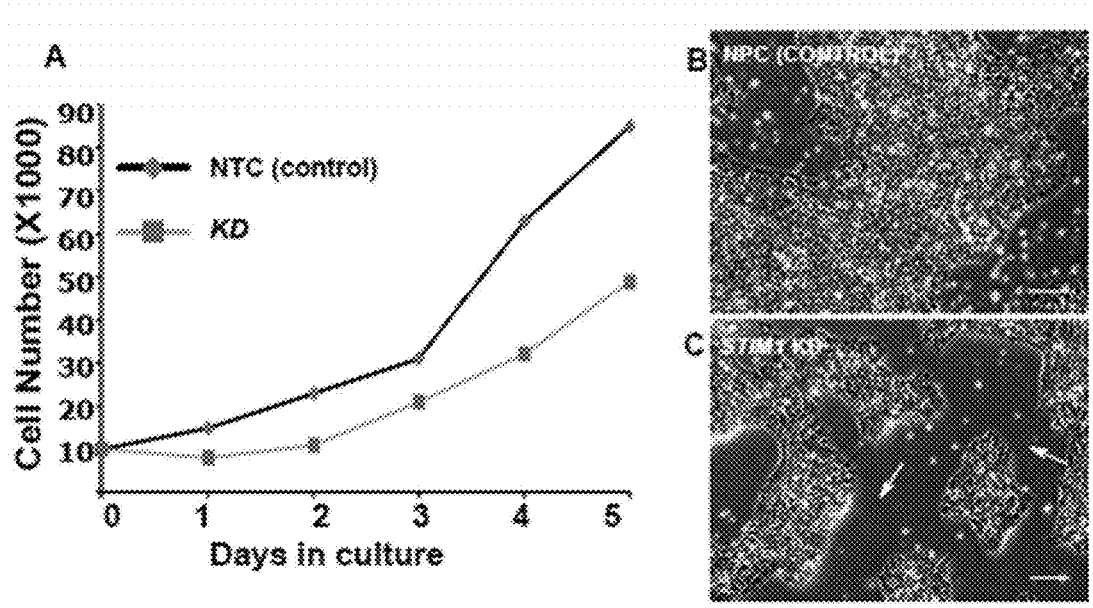

FIG. 6B illustrates STIM1 knockdown represses proliferation of iPSC-derived NPCs by Cell growth assays. (A) Growth curve of the control NTC and STIM1 knockdown NPCs grown as adherent monolayer at 5 DIV in triplicates, n=3. Morphology of (B) NTC, control cells and (C) STIM1 knockdown NPCs at 5 DIV. Arrows indicate spontaneous differentiation (neuronal projections). DIV-Days In Vitro, Scale bars are 50 μm.

Figure 7A:
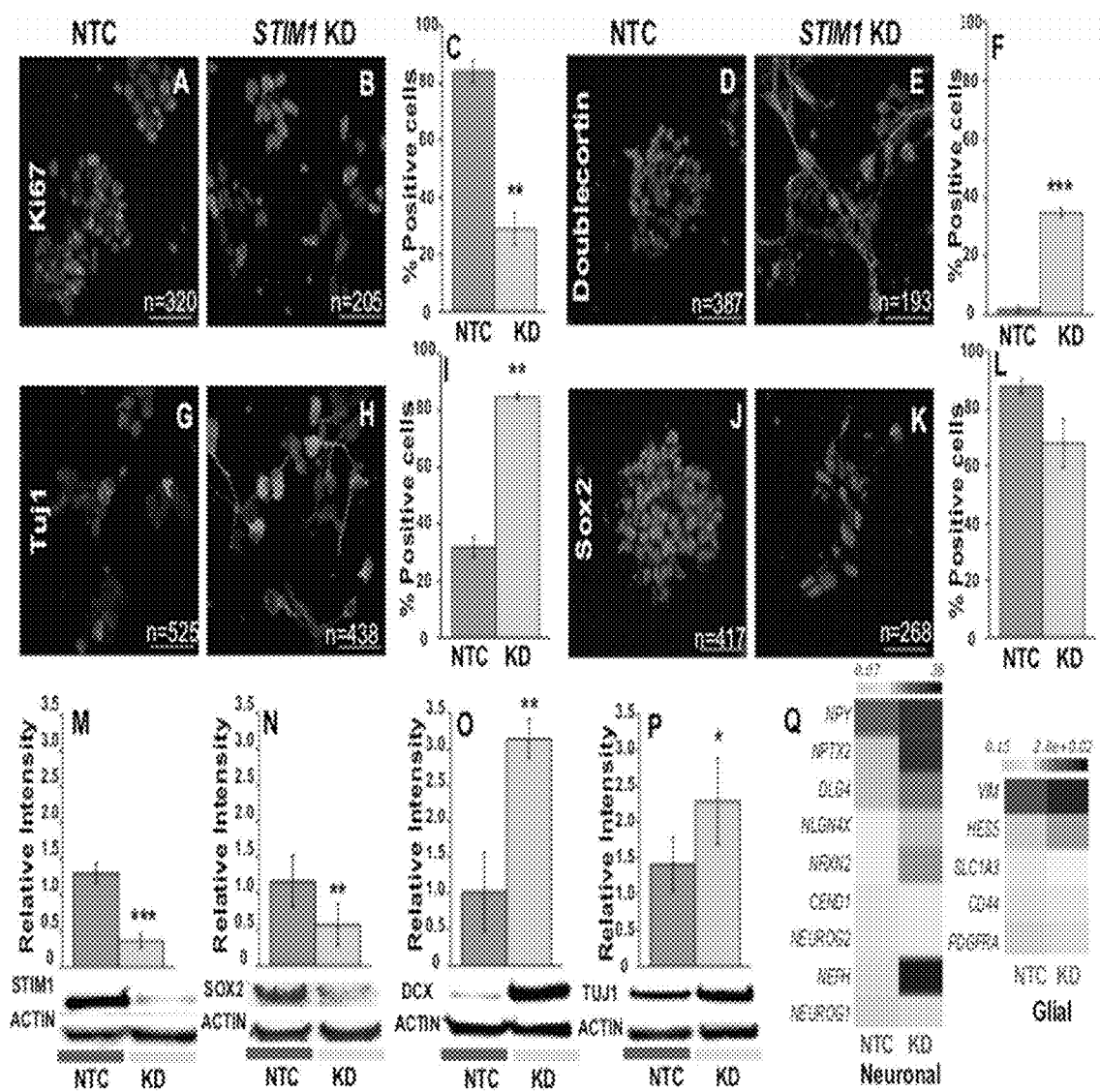

FIG. 7A illustrates STIM1 knockdown in NPCs promotes early neurogenesis. Immunostaining and western blot analysis of multipotent and differentiation markers (A, B) Immunostaining of the control and STIM1 knockdown NPCs for the proliferation marker Ki-67 and (C) its quantification as shown in the graph (p=0.0043) (D, E) Expression of Doublecortin (DCX) a marker of newly born neurons in the NTC and STIM1 knockdown NPCs and (F) its quantification as shown in the graph (p=1.67×10−4)(G, H) Neuron-specific Class III ß-tubulin (Tuj 1) in the NTC and STIM1 knockdown NPCs and (I) its quantification STIM1 as shown in the graph (p=0.0087) (J, K) Sox2, the multipotent neural stem cell marker the NTC and STIM1 knockdown NPCs and (L) its quantification as shown in the graph, not significant. Scale bar-50 μm. Total number of cells counted (n) as indicated in each panel. Western blot analysis showing (M) STIM1, p=0.0006 (N) Sox2, p=0.008 (0) DCX, p=0.0056 (P) Tuj 1 protein (p=0.043) levels in the control and knockdown cells (Q) Heat map representing normalized read counts of selected neuronal and glial genes which are up regulated in the knockdown NPCs. N=3, t-test used for all significance tests. Asterisks indicate *p<0.001, p<0.01, *p<0.05.

Figure 7B:
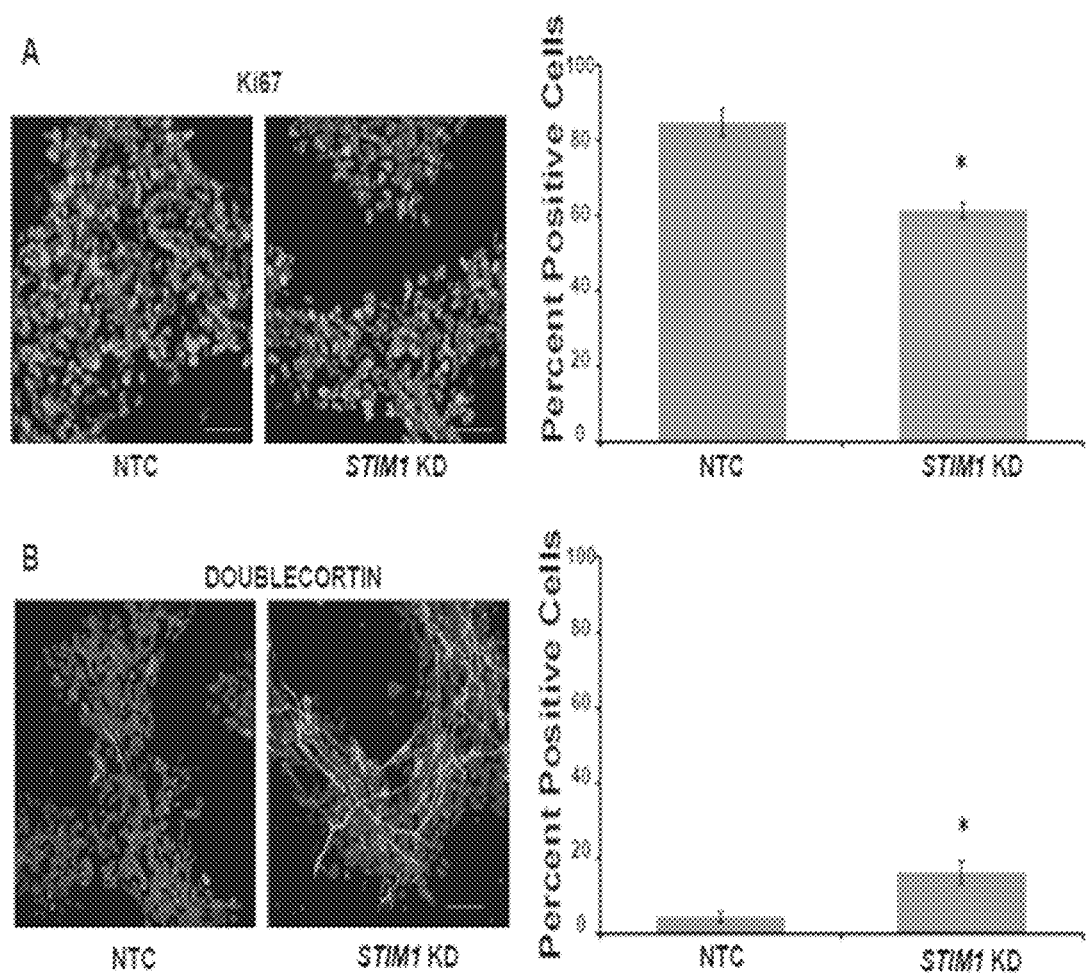

FIG. 7B illustrates STIM1 knockdown in iPSC-derived NPCs promotes early neurogenesis Immunostaining of the control and STIM1 knockdown NPCs for the proliferation marker Ki-67 and its quantification (Right) as shown in the graph (p=0.031) (B) Expression of Doublecortin (DCX) a marker of newly born neurons in the NTC and STIM1 knockdown NPCs and its quantification (Right) as shown in the graph (p=0.018).

EXAMPLE 1: STEPS OF EXPERIMENTAL DESIGN

FIG. 1 illustrates the experimental design of the present invention. Small molecule induced hNPCs are generated from a well-characterized human embryonic stem cell line (hESCs) H9/induced pluripotent stem cell (iPSC) line NIH1 and successfully knocked down STIM1, an essential element of SOCE, through lentiviral transduction to obtain expandable stable STIM1 knockdown hNPC cell lines. Small molecule derived hNPCs are transduced with STIM1 shRNA-miR. Ca$^{2+}$ imaging and immunoblots confirmed STIM1 knockdown and the attenuation of SOCE. To investigate cellular and molecular changes brought about by loss of SOCE RNAseq analyses of the STIM1 knockdown NPCs and their appropriate vector, controls are performed that helped to identify significant changes in gene expression. Changes in expression levels of selected genes, identified by RNAseq, are further validated by real-time PCR. To understand the functional significance of SOCE-regulated changes in gene expression, Gene Ontology analyses are performed and a set of enriched biological pathways were identified that underwent significant up or down-regulation. These pathways helped to design experiments for phenotypic/functional characterization of the STIM1 knockdown NPCs. Such experiments based on the identified GO pathways, corroborated a cell fate change in STIM1 knockdown NPCs. The statistics and p-value of the bioinformatics analyses and wet lab experiments are provided in the corresponding segments.

EXAMPLE 2: MAINTENANCE AND NEURAL INDUCTION OF HUMAN EMBRYONIC STEM CELLS (HESCS)

The hESC cell line comprising undifferentiated cells H9/WA09 (RRID: CVCL 9773) used for this study were initially cultured on irradiated mouse embryonic fibroblasts and gradually adapted to grow under feeder-free conditions by culturing on 0.5% Matrigel® in complete mTeSR™ media (Stem Cell Technologies, Vancouver, Canada). Passage of cells was initiated by washing with phosphate-buffered saline (PBS) followed by incubation at 37° C. in CTK dissociation solution (PBS containing 0.25% trypsin, 1 mg/mL collagenase IV, 20% KSR (all from Invitrogen, Carlsbad, CA, USA), and 1 mM $CaCl_2$) (Sigma, St Louis, MO, USA). hESC cultures were allowed to form embryoid bodies (EBs) by forced aggregation in low attachment dishes.

For neural induction, as described earlier two-day EBs were supplemented for neural induction with 10 mM SB431542 (Stem Cell Technologies), 1 mM dorsomorphin (Tocris Cookson, Ballwin, MO, USA), 3 mM CHIR99021 (Stem Cell Technologies) and 0.5 mM purmorphamine in suspension cultures. Four-day EBs were treated with 1:1 DMEM/F12 neurobasal medium supplemented with 1:200 N2, 1:100 B27 along with neural induction media factors in suspension cultures. Six-day EBs were plated onto Matrigel®-coated plates in maintenance medium containing 1:1 DMEM/F12 neurobasal medium supplemented with 1:200 N2, 1:100 B27, 3 µM CHIR99021, 0.5 mM purmorphamine and 150 µM ascorbic acid (Sigma, St Louis, MO, USA). Neural precursor cells (NPCs) were then passaged enzymatically with Accutase™ (Invitrogen) and freeze thawed as per requirement (protocol adapted from Reinhardt et al. 2013). NPCs could be maintained for >25 passages. For spontaneous differentiation, neural precursors were allowed to grow in media without small molecules only in the presence of $N_2$ and B27 supplements for 14-21 days. Media was replenished every alternate day for NPCs and spontaneously differentiating cultures.

Induced pluripotent stem cell (iPSC) line NIH1 were also used alternatively for generating human NPCs for the present invention.

FIG. 2 illustrates the derivation of hNPCs from the hESC. FIG. 2A illustrates the same as described above from iPSC.

EXAMPLE 3: SHRNA-MIRS AND LENTIVIRAL TRANSDUCTION FOR STIM1 KNOCKDOWN

ShERWOOD-UltramiR short hairpin RNA (shRNA), are vector-based RNAi that triggers with a new generation shRNA-specific design and an optimized microRNA scaffold "UltramiR". STIM1 knock-down was performed using a mixture of STIM1-ULTRA-3374033 (TAATAT-TGCACCTCCACCTCAT-SEQ. ID. NO.:1), ULTRA-3374029 (TTTATGATCTACATCATCCAGG)-SEQ. ID. NO.: 2) and ULTRA-3374031 (TCCAGTGAGTG-GATGCCAGGGT SEQ. ID. NO.:3) (transOMIC Technologies, Hunstsville) in NPCs. The mixture of all 3 shRNAs when used for the study was found to surprisingly achieve high transduction efficiency along with desired knockdown of protein. A non-targeting shRNA construct was used as a control for all experiments. The inducible ZIP (all-in-one) vector contains the components necessary for regulated expression of the shRNA-mir, including the TRE3GS inducible promoter positioned upstream of the shRNA, and the Tet-On 3G transcriptional activator (Tet-On 3G TA), which is expressed constitutively from an internal promoter. The Tet-On 3G TA binds to the TRE3GS promoter in the presence of Doxycycline and induces expression of ZsGreen and the shRNA-mir. This allows for direct visual confirmation of induced shRNA expression. A puromycin resistance gene (PuroR) is also encoded for rapid selection of transduced cells. The lentiviral transfer vector (pZIP) was co-transfected with the desired packaging vectors (pCMV-dR8.2 and pCMV-VSVG from Addgene RRID: SCR 002037) encoding the env, gag and pol protein into a packaging cell line (HEK293T-ATCC Cat #CRL-3216, RRID:CVCL 0063). The transfer vector contained sequences that packages as the viral genome and code for the shRNA-mir against STIM1 and selection cassette that integrates into the target cell's genome. Viral particles released from the packaging cell were harvested from the supernatant of the packaging cell for three days. The resulting viral supernatant was filtered through a 0.4511m PVDF syringe filters (Millipore), concentrated using a Lenti-X-concentrator, tested with a Lenti-X™ GoStix™ (Clontech) and applied to NPCs. After 24 hrs the media was discarded and fresh media with Doxycycline was added to induce shRNA expression. An MOI of 10 was used for the study. NPCs at P-10 were transduced with the viruses and at least 5 passages (with Doxycycline) were allowed to pass to obtain a stable knockdown NPC cell line.

Human NPCs transduced with a non-targeting vector control (NTC) were used as controls for all subsequent experiments. Western blot analyses confirmed maximal STIM1 knockdown (>90%, p=0.00067) in NPCs transduced with a pool of three STIM1 targeting shRNAs. Subsequent experiments were performed with NPCs at P18-P22. NPCs with STIM1 knockdown (referred to as STIM1 knockdown henceforth) exhibited a significant reduction in SOCE as compared to the corresponding control whereas release of store $Ca^{2+}$, after inhibition of the sarco-ER $Ca^{2+}$-ATPase by thapsigargin treatment, appeared similar to control cells (FIG. 3A). This was reproducible in the iPSC-derived NPCs also as illustrated in FIG. 3B. The mean basal cytosolic calcium levels of the control and STIM1 knockdown cells were 38 nM and 32 nM respectively. Thus, STIM1 knockdown causes a small but statistically significant reduction in basal [$Ca^{2+}$]. shRNA-miR against STIM1 has been purchased from a transOMIC Technologies, Huntsville, USA.

EXAMPLE 4: SOCE IN HNPCS AND ITS ATTENUATION WITH STIM1 SHRNA-MIR

To determine whether small molecule-derived NPCs exhibit SOCE, ER stores were depleted using 10 µM thapsigargin (TG), an inhibitor of the sarco-endoplasmic reticulum $Ca^{2+}$ ATPase pump in a $Ca^{2+}$-free solution and studied $Ca^{2+}$ influx after re-addition of extracellular 2 mM $Ca^{2+}$. ER-store $Ca^{2+}$ release followed by SOCE after re-addition of external $Ca^{2+}$ was revealed consistently across several passages in human NPCs. CRAC channels (calcium release-activated channels), identified as Orai1 and distinguished by high $Ca^{2+}$ selectivity and a unique pharmacological profile function in mouse NPCs as Store-Operated Calcium channels (Somasundaram et al., 2014). Therefore, it was tested if potent CRAC channel inhibitors like BTP-2 and 2-aminoethoxy-diphenyl borate (2-APB, Prakriya and Lewis, 2001) affect SOCE in human NPCs. Both BTP-2 (Bootmann et al., 2002) and 2-APB significantly inhibited SOCE in human NPCs. Thus, the pharmacological profile of SOCE in human NPCs is consistent with that of CRAC channels and resembles SOCE in primary mouse NPCs. FIG. 3A represents that knock down STIM1 attenuates SOCE in human NPCs derived from hESC whereas FIG. 3B represent that knock down STIM1 attenuates SOCE in human NPCs derived from iPSC.

EXAMPLE 5: TRANSCRIPTIONAL PROFILING OF STIM1 KNOCKDOWN NPCS

To identify potential gene expression changes by STIM1 knockdown in human NPCs, several parameters were analysed: parallel genome-wide analysis of mRNA expression profiles in non-transduced NPCs, non-targeting vector control (NTC) and the STIM1 knockdown NPCs. Stable knockdown of STIM1 lead to global transcriptional changes as evident by the clustering together of non-transduced NPCs with the NTC, whereas the STIM1 knockdown formed a separate cluster as observed using Jensen-Shannon divergence as a metric. Three independent methods, CuffDiff, EdgeR and DESeq were used for differential expression analysis and by overlap of genes identified in the three methods further analysis of 115 upregulated genes and 208 down-regulated genes was done. Thus, genes obtained by the intersection of all three methods were considered as the differentially expressed genes (DEGs) in the STIM1 knockdown NPCs. To understand if STIM1 knockdown modulates expression of STIM2 and the SOCE channel Orai, we looked at the FPKM values of these genes and confirmed that STIM1 was the only gene that was significantly down-regulated. The nature of biological processes that might be affected by STIM1 knockdown was predicted next by analysis of the differentially expressed genes (DEGs). Upregulated genes associated with biological processes such as signal transduction, regulation of nucleic acid metabolism and energy pathways, whereas down-regulated genes clustered with metabolism, cell growth and maintenance, and cell communication. Genes regulating cellular transport were both up- and down-regulated. The down-regulated processes appeared consistent with a less proliferative state, whereas the upregulated processes suggested increased cellular specialization and differentiation. To understand the nature of signaling mechanisms regulated by STIM1 in hNPCS, DAVID was used to assess the Gene Ontology (GO) of DEGs. Biological pathways that were significantly upregulated in STIM1 knockdown NPCs relative to control NTCs appeared consistent with neuronal differentiation and included nervous system development (GO:0007399), membrane depolarization (GO:0051899), neuron cell-cell adhesion (GO:0007158) and chemical synaptic transmission (GO:0007268). Conversely, significantly down-regulated pathways in STIM1 knockdown NPCs suggested reduced cell proliferation and included rRNA processing (GO: 0006364), cell proliferation (GO:0008283), G1/S transition of mitotic cell cycle (GO:0000082) and DNA replication (GO:0006260). FIG. 4 illustrates the analysis of Transcriptome of knock down STIM1

These data support the hypothesis that STIM1 knockdown in the NPCs reduces their proliferative and self-renewal capacities and concomitantly induces premature neural differentiation.

EXAMPLE 6: STIM1 KNOCKDOWN LEADS TO DECREASED PROLIFERATION AND EARLY NEUROGENESIS OF NPCS

Based on analysis of the RNAseq data, the morphology and proliferative potential of STIM1 knockdown NPCs were studied. The STIM1 knockdown cells exhibited rapid spontaneous differentiation evident as branched neurites and sparse cell clustering. The control NTC cells however resembled wild type NPCs. Their growth rates were similar to that of wild type cells (~24h population doubling time, passaged every 3-4 days). In contrast STIM1 knockdown NPCs cultures took much longer (>7 days) to become confluent. Presumably this is because cells committed to a more differentiated phenotype were lost on passaging and the remaining undifferentiated NPCs repopulated the culture more slowly, owing to their reduced numbers. To obtain a measure of the self-renewal capacity of STIM1 knockdown cells as compared to NTCs, both were tested by a neurosphere formation assay. Neural stem cells are known to continuously divide in culture to generate non-adherent spherical clusters of cells, commonly referred to as neurospheres when appropriate plating densities are established. At 48 hrs neurospheres were visible in both NTCs and STIM1 knockdown cultures; however it was evident that neurosphere size was greatly reduced in the STIM1 knockdown condition. This impaired proliferation was measured by counting neurospheres generated after a week in culture. Greater than 50% reduction of neurosphere numbers was observed in the STIM1 knockdown cells. Moreover neurospheres that formed in the NTC cultures were larger in size (180.0±8.3 μm), irrespective of the general heterogeneity in sphere sizes across cultures, as compared with neurospheres in STIM1 knockdown cultures (76.0±4.32 μm). The percentage of bigger spheres also appeared reduced in STIM1 knockdown cells. Very small spheres (<50 μm) in both conditions were not scored. It is evident from these experiments that the clonogenic and proliferative capacities of human NPCs are impaired upon STIM1 knock down (FIG. 5 and FIG. 6 illustrate the morphological and proliferation rate changes in STIM1 knockdown hNPCs).

Premature differentiation and the reduced proliferative potential of STIM1 knockdown NPCs were further assessed by immunostaining with appropriate markers (FIG. 7). Premature differentiation and the reduced proliferative potential of STIM1 knockdown NPCs from iPSC is shown in FIG. 6B and FIG. 7B.

STIM1 knockdown in human NPCs induces early neurogenesis that would eventually deplete the NPC pool. Indeed, transcript levels of many neuronal (NPY, NPTX2, DLG4, NLGN4X, NRXN2, CEND1, NEFH, NEUROG2, NEUROG1) and some early glial markers (HESS, SLC1A3, CD44, PDGFRA) were also significantly upregulated in the STIM1 knockdown NPCs as evident from RNAseq data (GSE109111). Physiologically NPCs/NSCs need to fine-tune quiescence and proliferation/commitment to guarantee lifelong neurogenesis and avoid premature exhaustion. Knock-down of STIM1 appears to tip this balance and push the cells towards a differentiated phenotype.

EXAMPLE 7

A. $Ca^{2+}$ Imaging in hNPCs:

Quantification of basal cytosolic $[Ca^{2+}]$ from hNPCs was performed using the dual-excitation single emission ratiometric $Ca^{2+}$-indicator Fura-2-AM. hNPCs plated as single adherent cells on PDL-coated coverslips were washed thrice with culture medium, following which they were loaded with 504 Fura-2-AM in dark for 45 mins at room temperature. The dye was dissolved in the culture medium supplemented with 0.002% Pluronic F-127. After dye loading, cells were washed thrice with culture medium. The culture medium was finally replaced with HBSS containing 2 mM Ca 2+(20 mM HEPES, 137 mM NaCl, 5 mM KCl, 10 mM Glucose, 1 mM MgCl2, 2 mM CaCl2, pH=7.3). Fura-2 was excited using dual 340/380 nm excitation and the emission intensity was recorded at 510 nm. Basal changes in cytosolic $Ca^{2+}$ were recorded for 10 frames at an interval of 5s. After this, 10 mM EGTA was added to obtain the minimum fluorescence values obtained after chelating all the available cytosolic $Ca^{2+}$ following which fluorescence changes were recorded every 5s for 85 frames. Subsequently, the extracellular medium was supplemented with 10 mM $Ca^{2+}$ and the maximum fluorescence intensity was recorded after saturating the dye loaded within the cell with $Ca^{2+}$ by adding 10 µM Ionomycin. Images were acquired after Ionomycin addition for 20 frames at 5s interval. The peak fluorescence value was generally obtained within the first 2 frames (corresponding to 10s) of Ionomycin addition. The emission intensities corresponding to excitation at 340 nm and 380 nm were used to calculate the F340/380 ratio for each cell across all the time points. The basal F340/380 at the start of imaging (t=0) was calibrated to $[Ca^{2+}]$ using the Grynkiewicz equation $$[Ca^{2+}](nM) = K_d \times \beta \times (R - R_{min})/(R_{max} - R),$$

where, Rmin and Rmax corresponds to the minimum F340/380 and maximum F340/380 obtained after EGTA and Ionomycin addition, respectively. K d for Fura-2 in human cells=~225 nM. ß (Scaling factor) is the ratio of the fluorescence emission intensities of the $Ca^{2+}$-free and the $Ca^{2+}$-bound forms of the dye after excitation at 380 nm. ß=5.

B. Library Preparation, Sequencing and RNASEQ Data Analysis

Total RNA was isolated from hNPCs using TRIzol as per manufacturer's instructions.

The RNA was run on a Bio-analyzer chip (Agilent) to ensure integrity. Approximately 500 ng of total RNA was used per sample to prepare libraries (RIN values>9) using a TruSeq™ RNA Library Prep Kit v2 (Illumina) following manufacturer's instructions. The prepared libraries were run on a DNA1000 chip of a Bio-analyzer to check their size. Libraries were then quantified by qPCR and run on an Illumina Hiseq® 2500 platform, for a single end and 75 bp read protocol (SciGenom, India).

Nine samples were run in a single lane. Biological triplicates were performed for each sample consisting of RNA isolated from wild type NPCs, shRNA control NPCs (referred to as the Non-Targeting Control or NTC) and STIM1 knockdown NPCs.

More than 100 million reads were obtained per sample with a uniform distribution of reads across samples (FIG. 4B). Reads (FASTQ sequences) obtained after sequencing were aligned to the annotated UCSC human genome (GRCh37/hg19) using HISAT2, RRID: SCR_015530 (Version-2.0.5). These aligned SAM files were converted to BAM files using SAM tools (Version-1.3) The resulting alignment data from SAM tools were then fed to CuffDiff2, RRID: SCR_001647, a software package that takes the reads aligned in BAM format as input, and uses geometric normalization on gene-length normalized read counts (FPKM, fragments per kilo base of exon per million reads), a beta negative binomial model for distribution of reads and t-test for calling differentially expressed genes. A corrected p-value was set, referred to as the q-value cut-off of 0.05 and Fold change >1=1.5(+/−) to identify differentially expressed genes by this method. Read counts for each transcript or exon were also calculated independently using python based package HTSeq (Version 0.9.1) (Anders et al., 2015). These read counts were then used as inputs for the differential analysis with DESeq, RRID:SCR_000154 and EdgeR, RRID:SCR_012802 (Anders and Huber, 2010; Robinson et al., 2010) empirical analysis of digital gene expression in R), two R based Bioconductor software that analyses the read counts per transcript per sample and normalizes (genes having very low read counts were removed) them using the Trimmed Mean of M-values (TMM) method and then fitting the values in a negative binomial model with variance and mean linked by local regression to identify differentially expressed genes. A fold change of 1.5(+/−) and p-value of 0.05 in DESeq and FDR p-value of 0.05 was set as cut-off in EdgeR. Genes found to be significantly altered by all the three different differential gene expression analysis methods were considered further. Significantly up and down regulated genes were subjected separately to a gene ontology based gene enrichment analysis tool, DAVID (Version 6.8) (Database for Annotation, Visualization and Integrated Discovery) and FunRich (Pathan et al., 2015) (Functional Enrichment analysis tool) using the human genome as the background gene set. In DAVID after converting the input gene IDs to corresponding DAVID gene IDs, the Functional Annotation Tool was used to carry out gene enrichment analysis based on the DAVID knowledge base. Fisher Exact P Value method was employed to measure the gene-enrichment in DAVID with a P value cut-off of 0.1 and the count threshold kept at 2 to speculate maximum information. Most significant biological pathways (GO level 5) enriched in DAVID have been reported as bar graphs. Gene enrichment analysis was also performed using the human Gene Ontology database, HPRD2 and FunRich (Pathan et al., 2015). Selected biological processes were identified by FunRich based on the presence of a higher percentage of genes (>6%). The genes enriched in each identified pathway have been represented as heat maps based on the FPKM values of the individual genes. The density box plot and dendrogram were generated using CummeRbund, RRID:SCR_014568 (Goff et al., 2012). Heat maps were generated using Matrix2png, RRID: SCR_011614.

(Pavlidis and Noble, 2003) and HemI (Heatmap Illustrator, Version 1.0.3.7) (Deng et al., 2014). Comparison of significantly altered gene lists from CuffDiff, DESeq and EdgeR and generation of Venn Diagrams were performed using FunRich. The data discussed in this publication have been deposited in NCBI's Gene Expression Omnibus (Edgar et al., 2002) and are accessible through GEO Series accession number GSE109111.

Table 1: Illustrates Biological pathways enriched by DAVID in STIM1 KD hNPCs. Top biological pathways up- and down-regulated in STIM1 KD NPCs vs control cells. Fisher Exact P-values are shown and GO terms are arranged according to their FDR value (False Discovery Rates). All over-represented pathways had a fold change >2. Both Benjamini Hochberg and Bonferroni multiple testing correction methods for the occurrence of false positive identifications by adjusting p-values are given. Shown are the gene lists identified in the data set and associated with each pathway. #indicates p-value>0.05.

TABLE 1

| GO TERM | PATHWAY | P-VALUE | FOLD ENRICHMENT | BONFERRONI | BENJAMINI | FDR | GENES |
|---|---|---|---|---|---|---|---|
| GO:0007268 | Chemical Synaptic Transmission | 6.96E-05 | 6.491 | 0.038 | 0.019 | 0.101 | NRXN2, KIF5A, NPTX2, GRIK4, DLG4, CHRNA4, PRKCG, CACNB3, CACNA1B |
| GO:0007158 | Neuron Cell-Cell Adhesion | 0.003 | 32.458 | 0.876 | 0.407 | 5.265 | NRXN2, NLGN4X, ASTN1 |
| GO:0051899 | Membrane Depolarization | 0.008 | 20.773 | 0.993 | 0.637 | 12.289 | CHRNA4, CACNB3, CACNA1B |
| GO:0030534 | Adult Behavior | 0.009 | 19.974 | 0.995 | 0.598 | 13.201 | NRXN2, NLGN4X, SHANK1 |
| GO:0007411 | Axon Guidance | 0.013 | 5.443 | 0.999 | 0.656 | 17.590 | KIF5A, NGFR, UNC5C, CHL1, SLIT3 |
| GO:0060997 | Dendritic Spine Morphogenesis | #0.066 | 28.852 | 1.0 | 0.950 | 63.527 | DLG4, SHANK1 |
| GO:0007399 | Nervous System Development | #0.082 | 3.015 | 1.0 | 0.933 | 71.593 | IGSF8, CPLX2, DLG4, SPOCK1, ELAVL3 |
| DOWNREGULATED | | | | | | | |
| GO:0006364 | rRNA Processing | 1.62E-07 | 6.130 | 2.21E-04 | 2.21E-04 | 2.66E-04 | EMG1, PNO1, EXOSC5, RPS27L, DIEXF, MRTO4, NOP14, EBNA1BP2, PA2G4, DKC1, DHX37, DDX21, PES1, LTV1, WDR43 |
| GO:0008283 | Cell Proliferation | 1.00E-06 | 4.301 | 0.001 | 6.82E-04 | 0.001 | POLR3G, TP53, CD70, MCM10, PRDX1, CDC25A, PLCE1, PA2G4, DKC1, ASCC3, FRAT2, TXNRD1, NRG1, LRP2, PES1, MYC, EMP1, GNL3 |
| GO:0000082 | G1/S Transition Of Mitotic Cell Cycle | 2.43E-06 | 8.574 | 0.003 | 0.001 | 0.003 | CCNE1, CDC6, CDC45, CDKN1A, RRM2, ID4, CDK6, RCC1, MCM10, CDC25A |
| GO:0006260 | DNA Replication | 4.01E-04 | 5.078 | 0.420 | 0.127 | 0.655 | EXO1, CDC6, CDC45, POLE3, RRM2, MCM10, C10ORF2, CDC25A, DSCC1 |
| GO:0042771 | Intrinsic Apoptotic Signaling Pathway In Response To DNA Damage By p53 Class Mediator | 4.01E-04 | 14.106 | 0.420 | 0.103 | 0.656 | CDKN1A, AEN, TP53, RPS27L, PHLDA3 |

EXAMPLE 8: QUANTITATIVE REAL TIME PCR

RNA was isolated from cells using TRIzol as per manufacturer's instructions. Quantity of the isolated RNA was estimated by a NanoDrop™ spectrophotometer (Thermo Scientific).

Approximately 1 μg of total RNA was used per sample for cDNA synthesis. Three or more independently isolated RNA samples were tested for validation of gene expression by quantitative PCR. Total RNA was treated with 0.5 U of DNase I (amplification grade) in a reaction mixture (22.1 μl) containing 1 mM DTT and 20U of RNase inhibitor. The reaction mixture was kept at 37° C. for 30 min followed by heat inactivation at 70° C. for 10 min. To this, 200U of MMLV reverse transcriptase, 50 μM random hexamers, and 1 mM dNTPs were added in a final volume of 25111 for cDNA synthesis. The reaction mixture was kept at 25° C. for 10 min, then 42° C. for 60 min, and finally heat inactivated at 70° C. for 10 min. Quantitative real-time PCRs (qPCRs) were performed in a total volume of 10111 with Kapa SYBR® Fast qPCR kit (KAPA Biosystems) on an ABI 7500 fast machine operated with ABI 7500 software (Applied Biosystems). Duplicates were performed for each qPCR reaction. GAPDH was used as the internal control. The fold change of gene expression in any experimental condition relative to wild-type was calculated as $2^{-\Delta\Delta Ct}$, where $\Delta\Delta Ct=$ (Ct (target gene)–Ct (GAPDH)) from STIM1 knockdown cDNA–(Ct (target gene)–Ct (GAPDH)) from NTC cDNA. Four independent samples in addition to the samples used for the RNA-Seq were quantified for each gene. Statistical significance was determined by the unequal variance t-test. Primer sequences (F, forward primer and R, reverse primer) for each gene tested by qPCR are given below:

```
GAPDH    F-TCACCAGGGC TGCTTTTAAC TC   SEQ. ID. NO.: 4
         R-ATGACAAGCT TCCCGTTCTC AG   SEQ. ID. NO.: 5
```

| | | |
|---|---|---|
| STIM1 | F-CACACTCTTT GGCACCTFCC | SEQ. ID. NO.: 6 |
| | R-TGACAATCTG GAAGCCACAG | SEQ. ID. NO.: 7 |
| UNC5C | F-ACGATGAGGA AAGGTCTGCG | SEQ. ID. NO.: 8 |
| | R-AAGTCATCAT CTTGGGCGGC | SEQ. ID. NO.: 9 |
| ELAVL3 | F-CAAGATCACA GGGCAGAGC | SEQ. ID. NO.: 10 |
| | R-ACGTACAGGT TAGCATCCCG | SEQ. ID. NO.: 11 |
| DLG4 | F-ACCAAGATGA AGACACGCCC | SEQ. ID. NO.: 12 |
| | R-CCTGCAACTC ATATATCCTG GGG | SEQ. ID. NO.: 13 |
| NFAT4 | F-CCGTAGTCAA GCTCCTAGGC | SEQ. ID. NO.: 14 |
| | R-TCTTGCCTGT GATACGGTGC | SEQ. ID. NO.: 15 |
| LIN28A | F-AAGAAGTCAG CCAAGGGTCT G | SEQ. ID. NO.: 16 |
| | R-CACAGTTGTA GCACCTGTCT C | SEQ. ID. NO.: 17 |
| BAX | F-CGGGGTTTCA TCCAGGATCG | SEQ. ID. NO.: 18 |
| | R-CGGCAATCAT CCTCTGCAGC | SEQ. ID. NO.: 19 |

Thus the present invention provides for the first time human neural precursor cells line comprising lentiviral transduced Dox inducible STIM1 knockdown. The STIM1 knockdown hNPcells are useful for investigating STIM1 function and SOCE in neurodevelopmental, neurodegenerative and psychiatric disorders and generating novel therapeutic insights. The said hNPCs cell lines comprising selectively Dox inducible knockdown STIM1 are helpful to study disorders with aberrant NPC regulation such as Rett's syndrome, schizophrenia. The glial cells and neurons differentiated form said hNPCs with STIM1 knockdown are helpful to study late stage disorders such as Parkinson's disease, Alzheimer's disease and Huntington's disease.

The invention claimed is:

1. A process for transducing human neural precursor cells (hNPCs) or human neural precursor cell lines with lentiviral constructs for knockdown of STIM1 expression by shRNA comprising:
   providing a lentiviral transfer vector containing sequences that package as a viral genome and encode for the shRNA for knockdown of STIM1 expression, wherein the sequences encoding the shRNA comprises TAATATTGCACCTCCACCTCAT (SEQ ID NO: 1), TTTATGATCTACATCATCCAGG (SEQ ID NO:2), and TCCAGTGAGTGGATGCCAGGGT (SEQ ID NO: 3);
   co-transfecting the lentiviral transfer vector with lentivirus-based second generation packaging vectors encoding env, gag and pol protein into a packaging cell line for releasing viral particles therefrom;
   harvesting the viral particles that contain the sequences that package as a viral genome and encode for the shRNA for knockdown of STIM1 expression from the supernatant of the packaging cell line;
   providing human neural precursor cells (hNPCs) or human neural precursor cell lines; and
   carrying out gene expression modulation of said human neural precursor cells (hNPCs) or human neural precursor cell lines by applying the harvested viral particles to said human neural precursor cells (hNPCs) or human neural precursor cell lines and inducing shRNA expression for knockdown of STIM1 expression, thereby regulating intracellular calcium signaling and decreasing Store Operated Calcium Entry (SOCE).

2. The process of claim 1, wherein said human neural precursor cells (hNPCs) or human neural precursor cell lines are derived from pluripotent stem cell lines selected from human embryonic stem cell line (hESCs) or human induced pluripotent stem cell line (hiPSC).

3. The process of claim 1, wherein the step of inducing shRNA expression comprises adding doxycycline.

4. The process of claim 1, wherein the step of inducing shRNA expression comprises passaging said human neural precursor cells (hNPCs) or human neural precursor cell lines for at least 5 passages with doxycycline.

* * * * *

SEQUENCE LISTING

```
<160> NUMBER OF SEQ ID NOS: 19

<210> SEQ ID NO 1
<211> LENGTH: 22
<212> TYPE: DNA
<213> ORGANISM: Artificial Sequence
<220> FEATURE:
<223> OTHER INFORMATION: ULTRA-3374033

<400> SEQUENCE: 1
taatattgca cctccacctc at                                          22

<210> SEQ ID NO 2
<211> LENGTH: 22
<212> TYPE: DNA
<213> ORGANISM: Artificial Sequence
<220> FEATURE:
<223> OTHER INFORMATION: ULTRA-3374029

<400> SEQUENCE: 2
tttatgatct acatcatcca gg                                          22

<210> SEQ ID NO 3
<211> LENGTH: 22
<212> TYPE: DNA
<213> ORGANISM: Artificial Sequence
<220> FEATURE:
<223> OTHER INFORMATION: ULTRA-3374031

<400> SEQUENCE: 3
tccagtgagt ggatgccagg gt                                          22

<210> SEQ ID NO 4
<211> LENGTH: 22
<212> TYPE: DNA
<213> ORGANISM: Artificial Sequence
<220> FEATURE:
<223> OTHER INFORMATION: Sequence of the forward primer for GAPDH

<400> SEQUENCE: 4
tcaccagggc tgcttttaac tc                                          22

<210> SEQ ID NO 5
<211> LENGTH: 22
<212> TYPE: DNA
<213> ORGANISM: Artificial Sequence
```

<220> FEATURE:
<223> OTHER INFORMATION: sequence of the reverse primer for GAPDH

<400> SEQUENCE: 5
atgacaagct tcccgttctc ag                                          22

<210> SEQ ID NO 6
<211> LENGTH: 20
<212> TYPE: DNA
<213> ORGANISM: Artificial Sequence
<220> FEATURE:
<223> OTHER INFORMATION: Sequence of the forward primer for STIM1

<400> SEQUENCE: 6
cacactcttt ggcaccttcc                                             20

<210> SEQ ID NO 7
<211> LENGTH: 20
<212> TYPE: DNA
<213> ORGANISM: Artificial Sequence
<220> FEATURE:
<223> OTHER INFORMATION: Sequence of the reverse primer for STIM1

<400> SEQUENCE: 7
tgacaatctg gaagccacag                                             20

<210> SEQ ID NO 8
<211> LENGTH: 20
<212> TYPE: DNA
<213> ORGANISM: Artificial Sequence
<220> FEATURE:
<223> OTHER INFORMATION: Sequence of the forward primer for UNC5C

<400> SEQUENCE: 8
acgatgagga aaggtctgcg                                             20

<210> SEQ ID NO 9
<211> LENGTH: 20
<212> TYPE: DNA
<213> ORGANISM: Artificial Sequence
<220> FEATURE:
<223> OTHER INFORMATION: Sequence of the reverse primer for UNC5C

<400> SEQUENCE: 9
aagtcatcat cttgggcggc                                             20

<210> SEQ ID NO 10
<211> LENGTH: 19
<212> TYPE: DNA
<213> ORGANISM: Artificial Sequence
<220> FEATURE:
<223> OTHER INFORMATION: Sequence of the forward primer for ELAVL3

<400> SEQUENCE: 10
caagatcaca gggcagagc                                              19

<210> SEQ ID NO 11
<211> LENGTH: 20
<212> TYPE: DNA
<213> ORGANISM: Artificial Sequence
<220> FEATURE:
<223> OTHER INFORMATION: Sequence of the reverse primer for ELAVL3

<400> SEQUENCE: 11
acgtacaggt tagcatcccg                                             20

```
<210> SEQ ID NO 12
<211> LENGTH: 20
<212> TYPE: DNA
<213> ORGANISM: Artificial Sequence
<220> FEATURE:
<223> OTHER INFORMATION: Sequence of the forwaard primer for DLG4

<400> SEQUENCE: 12
accaagatga agacacgccc                                                     20

<210> SEQ ID NO 13
<211> LENGTH: 23
<212> TYPE: DNA
<213> ORGANISM: Artificial Sequence
<220> FEATURE:
<223> OTHER INFORMATION: Sequence of the reverse primer for DLG4

<400> SEQUENCE: 13
cctgcaactc atatatcctg ggg                                                 23

<210> SEQ ID NO 14
<211> LENGTH: 20
<212> TYPE: DNA
<213> ORGANISM: Artificial Sequence
<220> FEATURE:
<223> OTHER INFORMATION: Sequence of the forward primer for NFAT4

<400> SEQUENCE: 14
ccgtagtcaa gctcctaggc                                                     20

<210> SEQ ID NO 15
<211> LENGTH: 20
<212> TYPE: DNA
<213> ORGANISM: Artificial Sequence
<220> FEATURE:
<223> OTHER INFORMATION: Sequence of the reverse primer for NFAT4

<400> SEQUENCE: 15
tcttgcctgt gatacggtgc                                                     20

<210> SEQ ID NO 16
<211> LENGTH: 21
<212> TYPE: DNA
<213> ORGANISM: Artificial Sequence
<220> FEATURE:
<223> OTHER INFORMATION: Sequence of the forward primer for LIN28A

<400> SEQUENCE: 16
aagaagtcag ccaagggtct g                                                   21

<210> SEQ ID NO 17
<211> LENGTH: 21
<212> TYPE: DNA
<213> ORGANISM: Artificial Sequence
<220> FEATURE:
<223> OTHER INFORMATION: Sequence of the reverse primer for LIN28A

<400> SEQUENCE: 17
cacagttgta gcacctgtct c                                                   21

<210> SEQ ID NO 18
<211> LENGTH: 20
<212> TYPE: DNA
<213> ORGANISM: Artificial Sequence
<220> FEATURE:
<223> OTHER INFORMATION: Sequence of the forward primer for BAX
```

```
<400> SEQUENCE: 18
cggggtttca tccaggatcg                                                   20

<210> SEQ ID NO 19
<211> LENGTH: 20
<212> TYPE: DNA
<213> ORGANISM: Artificial Sequence
<220> FEATURE:
<223> OTHER INFORMATION: Sequence of the reverse primer for BAX

<400> SEQUENCE: 19
cggcaatcat cctctgcagc                                                   20
```